(12) United States Patent
Blanke et al.

(10) Patent No.: US 12,629,072 B2
(45) Date of Patent: May 19, 2026

(54) METHOD AND SYSTEM FOR DETERMINING THE INTENTION OF PERFORMING A VOLUNTARY ACTION

(71) Applicant: ECOLE POLYTECHNIQUE FEDERALE DE LAUSANNE (EPFL), Lausanne (CH)

(72) Inventors: Olaf Blanke, Nyon (CH); Hyeongdong Park, Geneva (CH); Olivier Kannape, Morges (CH); Bastien Orset, Lausanne (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 836 days.

(21) Appl. No.: 17/791,913

(22) PCT Filed: Feb. 3, 2021

(86) PCT No.: PCT/IB2021/050851
§ 371 (c)(1),
(2) Date: Jul. 11, 2022

(87) PCT Pub. No.: WO2021/156753
PCT Pub. Date: Aug. 12, 2021

(65) Prior Publication Data
US 2023/0040401 A1 Feb. 9, 2023

(30) Foreign Application Priority Data
Feb. 4, 2020 (WO) .................. PCT/IB2020/050858

(51) Int. Cl.
A61B 5/16 (2006.01)
A61B 5/0205 (2006.01)
A61B 5/372 (2021.01)

(52) U.S. Cl.
CPC ............ *A61B 5/165* (2013.01); *A61B 5/0205* (2013.01); *A61B 5/372* (2021.01)

(58) Field of Classification Search
CPC ....... A61B 5/0205; A61B 5/165; A61B 5/369; A61B 5/372; A61B 5/374; A61B 5/4064
See application file for complete search history.

(56) References Cited

U.S. PATENT DOCUMENTS

2012/0226185 A1 9/2012 Chung
2013/0204150 A1* 8/2013 Similowski ....... A61M 16/0057
128/204.23

(Continued)

FOREIGN PATENT DOCUMENTS

WO 2019111257 A1 6/2019
WO WO 2019111257 6/2019

OTHER PUBLICATIONS

Ajne, B. (1968). A simple test for uniformity of a circular distribution. Biometrika, 55(2), 343-354.

(Continued)

*Primary Examiner* — Tse W Chen
*Assistant Examiner* — Michael A Catina
(74) *Attorney, Agent, or Firm* — Nixon & Vanderhye

(57) ABSTRACT

The invention relates to methods and systems for determining the intention of a subject to perform a voluntary action based on the analysis of the subject's respiratory phases and neuroelectrical signals.

10 Claims, 8 Drawing Sheets

(56) References Cited

U.S. PATENT DOCUMENTS

2016/0008559 A1*  1/2016  Tiedje ................. A61M 16/024
                                                            128/204.23
2021/0259601 A1   8/2021  Kornberg et al.

OTHER PUBLICATIONS

Allard, E., Canzoneri, E., Adler, D., Morélol-Panzini, C., Bello-Ruiz, J., Herbelin, B., . . . & Similowski, T. (2017). Interferences between breathing, experimental dyspnoea and bodily self-consciousness. Scientific reports, 7(1), 1-11.

Azevedo, R. T., Garfinkel, S. N., Critchley, H. D. , & Tsakiris, M. (2017). Cardiac afferent activity modulates the expression of racial stereotypes. Nature Communications, 8(1), 1-9.

Baek, K., Doñamayor, N., Morris, L. S., Strelchuk, D., Mitchell, S., Mikheenko, Y., . . . & Voon, V. (2017). Impaired awareness of motor intention in functional neurological disorder: implications for voluntary and functional movement. Psychological medicine, 47(9), 1624-1636.

Ball, T., Schreiber, A., Feige, B., Wagner, M., Lucking, C. H., & Kristeva-Feige, R. (1999). The role of higher-order motor areas in voluntary movement as revealed by high-resolution EEG and fMRI. Neuroimage, 10(6), 682-694.

Berens, P. (2009). CircStat: a MATLAB toolbox for circular statistics. Journal of statistical software, 31, 1-21.

Birn, R. M., Murphy, K., & Bandettini, P. A. (2008). The effect of respiration variations on independent component analysis results of resting state functional connectivity. Human brain mapping, 29(7), 740-750.

Bramble, D. M., & Carrier, D. R. (1983) . Running and breathing in mammals. Science, 219(4582), 251-256.

Del Negro, C. A., Funk, G. D., & Feldman, J. L. (2018). Breathing matters. Nature Reviews Neuroscience, 19(6), 351-367.

Evans, K. C., Shea, S. A. , & Saykin, A. J. (1999). Functional MRI localisation of central nervous system regions associated with volitional inspiration in humans. The Journal of Physiology, 520(2), 383-392.

Faull, O. K., Subramanian, H. H., Ezra, M., & Pattinson, K. T. (2019). The midbrain periaqueductal gray as an integrative and interoceptive neural structure for breathing. Neuroscience & Biobehavioral Reviews, 98, 135-144.

Fried, I., Mukamel, R., & Kreiman, G. (2011). Internally generated preactivation of single neurons in human medial frontal cortex predicts volition. Neuron, 69(3), 548-562.

Garfinkel, S. N., Minati, L., Gray, M. A., Seth, A. K., Dolan, R. J., & Critchley, H. D. (2014). Fear from the heart: sensitivity to fear stimuli depends on individual heartbeats. Journal of Neuroscience, 34(19), 6573-6582.

Garipelli, G., Chavarriaga, R., & Millán, J. D. R. (Apr. 2011). Single trial recognition of anticipatory slow cortical potentials: the role of spatio-spectral filtering. In 2011 5th International IEEE/EMBS Conference on Neural Engineering (pp. 408-411). IEEE.

Haggard, P. (2008). Human volition: towards a neuroscience of will. Nature Reviews Neuroscience, 9(12), 934-946.

Heck, D. H., McAfee, S. S., Liu, Y., Babajani-Feremi, A., Rezaie, R., Freeman, W. J., . . . & Kozma, R. (2017). Breathing as a fundamental rhythm of brain function. Frontiers in neural circuits, 10, 115.

International Search Report mailed on Jun. 9, 2021, for Application N° PCT/IB2021/050851.

Khalighinejad, N., Schurger, A., Desantis, A., Zmigrod, L., & Haggard, P. (2018). Precursor processes of human self-initiated action. Neuroimage, 165, 35-47.

Kornhuber, H. H., & Deecke, L. (1965). Changes in the brain potential in voluntary movements and passive movements in man: readiness potential and reafferent potentials. Pflugers Archiv fur die gesamte Physiologie des Menschen und der Tiere, 284, 1-17.

(Original Title Hirnpotentialänderungen bei Willkürbewegungen und nassiven Bewegungen des Menschen: Bereitschaftspotential und.

Kurnikova, A., Moore, J. D., Liao, S. M., Deschênes, M., & Kleinfeld, D. (2017). Coordination of orofacial motor actions into exploratory behavior by rat. Current Biology, 27(5), 688-696.

Lee, K., Liu, D., Perroud, L., Chavarriaga, R., & Millan, J. D. R. (2017) . A brain-controlled exoskeleton with cascaded event-related desynchronization classifiers. Robotics and Autonomous Systems, 90, 15-23.

Libet, B. (1985). Unconscious cerebral initiative and the role of conscious will in voluntary action. Behavioral and brain sciences, 8(4), 529-539.

Libet, B., Gleason, C. A., & Wright, E. W. (1983). Time of conscious intention to act in relation to onset of cerebral activity (readiness-potential). The unconscious initiation of a freely voluntary act. Brain, 106, 623-642.

McFarland, D. H. (2001). Respiratory markers of conversational interaction. Journal of Speech, Language, and Hearing Research; Feb. 2001; 44, 1; ProQuest Psychology Journals p. 128-143.

Mineva, A., & Popivanov, D. (1996). Method for single-trial readiness potential identification, based on singular spectrum analysis. Journal of neuroscience methods, 68(1), 91-99.

Mitrou, N., Laurin, A., Dick, T., & Inskip, J. (2017). A peak detection method for identifying phase in physiological signals. Biomedical Signal Processing and Control, 31, 452-462.

Moore, J. D., Deschênes, M., Furuta, T., Huber, D., Smear, M. C., Demers, M., & Kleinfeld, D. (2013). Hierarchy of orofacial rhythms revealed through whisking and breathing. Nature, 497(7448), 205-210.

Morawiec, E., Raux, M., Kindler, F., Laviolette, L., & Similowski, T. (2015). Expiratory load compensation is associated with electro-encephalographic premotor potentials in humans. Journal of applied physiology, 118(8), 1023-1030.

Murakami, M., Vicente, M. I., Costa, G. M., & Mainen, Z. F. (2014) . Neural antecedents of self-initiated actions in secondary motor cortex. Nature neuroscience, 17(11), 1574-1582.

Ohl, S., Wohltat, C., Kliegl, R., Pollatos, O., & Engbert, R. (2016). Microsaccades are coupled to heartbeat. Journal of Neuroscience, 36(4), 1237-1241.

Oostenveld, R., Fries, P., Maris, E., & Schoffelen, J. M. (2011). FieldTrip: open source software for advanced analysis of MEG, EEG, and invasive electrophysiological data. Computational intelligence and neuroscience, 2011.

Park, H. D., Bernasconi, F., Salomon, R., Tallon-Baudry, C., Spinelli, L., Seeck, M., . . . & Blanke, O. (2018). Neural sources and underlying mechanisms of neural responses to heartbeats, and their role in bodily self-consciousness: an intracranial EEG study. Cerebral Cortex, 28(7), 2351-2364.

Park, H. D., Correia, S., Ducorps, A., & Tallon-Baudry, C. (2014). Spontaneous fluctuations in neural responses to heartbeats predict visual detection. Nature neuroscience, 17(4), 612-618.

Paydarfar, D., Gilbert, R. J., Poppel, C. S., & Nassab, P. F. (1995). Respiratory phase resetting and airflow changes induced by swallowing in humans. The Journal of physiology, 483(1), 273-288.

Pfurtscheller, G., Ortner, R., Bauernfeind, G., Linortner, P., & Neuper, C. (2010). Does conscious intention to perform a motor act depend on slow cardiovascular rhythms?. Neuroscience letters, 468(1), 46-50.

Raux, M., Straus, C., Redolfi, S., Morelot-Panzini, C., Couturier, A., Hug, F., & Similowski, T. (2007). Electroencephalographic evidence for pre-motor cortex activation during inspiratory loading in humans. The Journal of Physiology, 578(2), 569-578.

Rebollo, I., Devauchelle, A. D., Béranger, B., & Tallon-Baudry, C. (2018). Stomach-brain synchrony reveals a novel, delayed-connectivity resting-state network in humans. Elife, 7, e33321.

Richter, C. G., Babo-Rebelo, M., Schwartz, D., & Tallon-Baudry, C. (2017). Phase-amplitude coupling at the organism level: the amplitude of spontaneous alpha rhythm fluctuations varies with the phase of the infra-slow gastric basal rhythm. NeuroImage, 146, 951-958.

Schultze-Kraft, M., Birman, D., Rusconi, M., Allefeld, C., Görgen, K., Dähne, S., . . . & Haynes, J. D. (2016). The point of no return

(56) References Cited

OTHER PUBLICATIONS in vetoing self-initiated movements. Proceedings of the national Academy of Sciences, 113(4), 1080-1085.

Schurger, A., Mylopoulos, M., & Rosenthal, D. (2016) . Neural antecedents of spontaneous voluntary movement: a new perspective. Trends in Cognitive Sciences, 20(2), 77-79.

Schurger, A., Sitt, J. D., & Dehaene, S. (2012) . An accumulator model for spontaneous neural activity prior to self-initiated movement. Proceedings of the National Academy of Sciences, 109(42), E2904-E2913.

Smotherman, M., Kobayasi, K., Ma, J., Zhang, S., & Metzner, W. (2006). A mechanism for vocal-respiratory coupling in the mammalian parabrachial nucleus. Journal of Neuroscience, 26(18), 4860-4869.

Tort, A. B., Brankačk, J., & Draguhn, A. (2018). Respiration-entrained brain rhythms are global but often overlooked. Trends in neurosciences, 41(4), 186-197.

Tort, A. B., Komorowski, R., Eichenbaum, H., & Kopell, N. (2010). Measuring phase-amplitude coupling between neuronal oscillations of different frequencies. Journal of neurophysiology, 104(2), 1195-1210.

Written Opinion of the ISA mailed on Jun. 9, 2021, for Application N° PCT/IB2021/050851.

Zelano, C., Jiang, H., Zhou, G., Arora, N., Schuele, S., Rosenow, J., & Gottfried, J. A. (2016). Nasal respiration entrains human limbic oscillations and modulates cognitive function. Journal of Neuroscience, 36(49), 12448-12467.

Office Action, issued in European Patent Application No. 21709467.1 dated Aug. 1, 2024.

* cited by examiner

METHOD AND SYSTEM FOR DETERMINING THE INTENTION OF PERFORMING A VOLUNTARY ACTION

CROSS REFERENCE TO RELATED APPLICATIONS

The present application is a United States national stage application of International patent application No. PCT/IB2021/050851 filed on Feb. 3, 2021 that designated the United States, and claims foreign priority to International patent application No. PCT/IB2020/050858 filed on Feb. 4, 2020, the contents of both documents being herewith incorporated by reference in their entirety.

TECHNICAL FIELD

The invention belongs to the fields of neurosciences and physiology. In particular, the invention relates to methods and systems for determining the intention of a subject to perform a voluntary action based on the analysis of the subject's respiratory phases and neuroelectrical signals.

BACKGROUND ART

Voluntary action control, the ability to initiate and execute an action based on one's own free will, is an essential component of self-consciousness (1, 2). More than fifty years ago, Kornhuber and colleagues reported that a slow negative drift of brain activity, the so-called readiness potential (RP), precedes the onset of voluntary action by ~1 second (3), a finding which has been replicated and confirmed by diverse electrophysiological methods including single cell recordings in humans (1) and animals (4). Together with Libet's seminal observation that the onset of the RP precedes participants' conscious intention of a movement (5), the RP has been interpreted as an unconscious cortical precursor to the conscious intention to perform an action (6). Recently, this decade-long interpretation has been challenged, with Schurger and colleagues proposing that the RP reflects spontaneous fluctuation of background neuronal activity or noise, rather than a specific neural process underlying the preparation of voluntary action (4, 7, 8, 9).

An important source of continuously changing neural signals—at the cortical, subcortical and peripheral level—are interoceptive signals, for example respiratory or cardiac signals. Recent research has shown that interoceptive signals and associated neural activity impacts sensory processes, including visual perception (10) and emotional processing (11), as well as involuntary movements such as micro-saccadic eye movements (12). Further work suggested that interoceptive neural processing contributes to ongoing neuronal activity at rest (13, 14, 15, 16) which has been suggested to be associated with RP generation (8, 9). Moreover, breathing control has been shown to be associated with cortical motor regions such as the supplementary motor area (SMA) (17), which also has been proposed as the primary source of the RP. Breathing is synchronized with locomotion in mammals (18) and whisking in rodents (19), collectively suggesting a potential interaction between breathing and the control of voluntary action. In humans, although few studies have measured respiration signals during voluntary movement tasks, it has rather been considered as physiological noise (20).

This is also true in the context of Brain-machine interfaces (BMI), computer-based systems that acquire brain signals, analyse them and translate them into commands that are relayed to an output device to carry out a desired action. Typically, when it comes to BMIs, only brain signals are considered and other biosignals, such as respiratory or cardiac signals, are treated as physiological noise. Despite this assumption, multiple studies have shown that combining such bodily signals to brain signals could improve the reliability of BMIs.

As of today, a potential link between respiration and voluntary action, as well as evidences on whether interoceptive bodily signals impact voluntary action and the associated RP, are still lacking. Defining such an association would be of paramount importance to unveil unconscious-to-conscious signal processing between internal bodily states and the person's voluntary actions; at the same time, providing a method to determine the intention of a subject to perform a voluntary action based on readily available respiratory signals would open a completely novel field of study and applications, for instance for the treatment of pathological medical conditions, human-machine interfaces and/or brain-machine interfaces, and more generally, the prediction of voluntary actions.

SUMMARY OF INVENTION

Based on previous research showing that internal bodily signals affect sensory processing and ongoing neural activity, the present inventors investigated the potential role of interoceptive signals on voluntary action, the conscious awareness thereof, and the RP or other neuroelectrical parameters such as event-related desynchronization ERD.

During those investigations the inventors have surprisingly found that respiration was the source of the apparently spontaneous fluctuations of background neuronal activity that have been linked to the RP. This finding was based on experiments where subjects were asked to perform two classical voluntary action tasks, the Kornhuber task (3, 21) and the Libet task (5), while recording their electroencephalographic (EEG) and electrocardiographic (ECG) signals, as well as respiration signals. The analysis was focused on the coupling between voluntary action and phase of cardiac and respiratory signals. It was shown that fluctuations of respiratory, but not cardiac, phase are coupled with the onset of voluntary action and the neural hallmark of voluntary action: the EEG-based RP.

Briefly summarizing, the inventors have been able to define a coupling between breathing and the initiation of voluntary action in human subjects, thereby providing evidence that 1) participants initiate voluntary actions more frequently during the expiration phase of a respiratory cycle, 2) this respiration-action coupling is absent during externally-triggered actions, and 3) the RP amplitude is modulated depending on the respiratory phase. These findings demonstrate that voluntary action is specifically coupled with the respiratory system and further suggest that the RP is associated with fluctuations of ongoing neural activity that are driven by the involuntary and cyclic motor act of breathing.

In parallel, the inventors aimed at investigating how breathing can affect the performance of Motor Imagery (MI) tasks as well as its corresponding correlates using Brain-machine interface (BMI) performance metrics and EEG neuroimaging techniques. To do so, a MI paradigm was designed with phase-locked starting cues linked to the breathing cycle (expiration-locked and inhalation-locked cues) and a non-breathing related phase-locked starting cue (time-based cues) in which subjects were instructed to perform a kinesthetic MI task.

It was shown that phase-locked inhalation cues lead to better performances in MI tasks compared to phase-locked exhalation cues. Moreover, it was shown that classical MI correlates, such as μ- and β-Event-Related Desynchronization (ERDs), are modulated by the respiratory phase similarly to when performing voluntary action with stronger MI correlates observed during late-phase exhalation. The inventors also provide evidence that BMI decoding performance is predicted from respiration rate changes and that BMI decoding is better during exhalation versus inhalation. These results suggest that observable changes in respiration rate can reliably predict BMI performance making breathing a reliable indicator regarding BMI performance.

Based on those unexpected observations the inventors have developed a method for determining the intention of performing a voluntary action in a subject. This method constitutes the object of claim 1.

Another object of the present invention relates to a system according to claim 8.

Further embodiments of the present invention are defined by the appended claims.

The above and other objects, features and advantages of the herein presented subject-matter will become more apparent from a study of the following description with reference to the attached figures showing some preferred aspects of said subject-matter.

(c) Histogram of the summed statistics (i.e., minimum number of data points that can be observed in half of the circle; Hodges-Ajne test) obtained from surrogate respiration data. The blue vertical line indicates the summed statistics from original respiration data. A computed test statistics using original data was significantly smaller than a chance level statistics obtained from phase shifted surrogate respiration data (permutation p=0.0009), confirming the timing of button presses in Experiment-1 is coupled with the respiratory phase.

Figure 2:
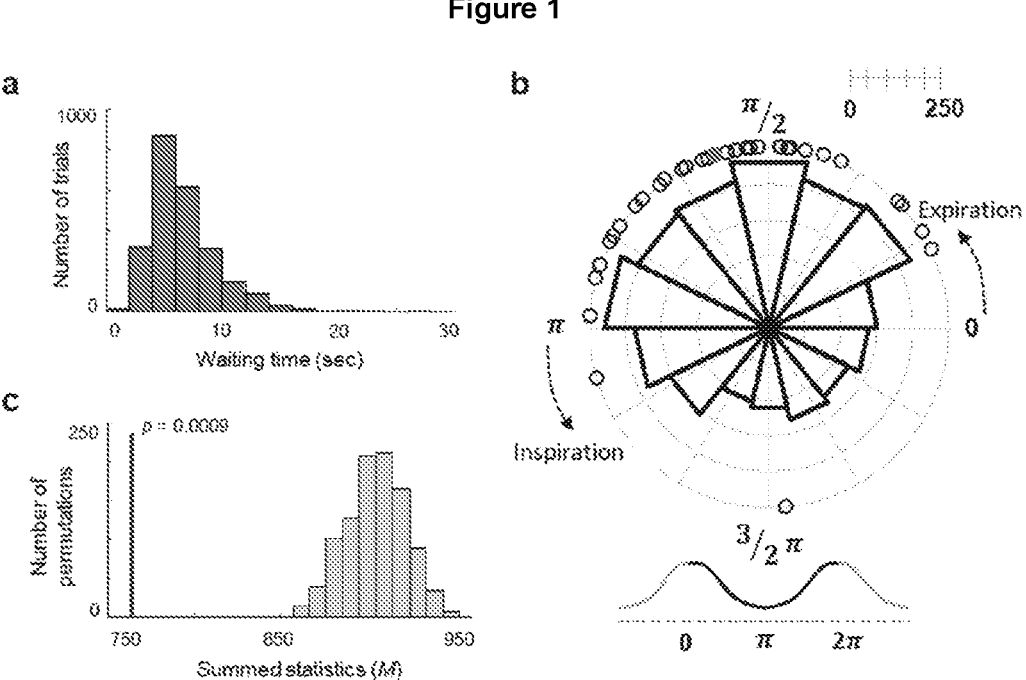

FIG. 2. Coupling between voluntary action and respiratory phase during the Libet task in Experiment-2. (a) Distribution of waiting times (pooled across 32 participants) showed the typical rightward skewed shape. (b) Distribution of respiration phases with respect to the timing of voluntary action onset. Empty black circles represent each participant's mean respiration phase at button press. Participants initiated voluntary actions more frequently during the expiration phase. The polar histogram shows the distribution of all the button presses from 32 participants, which was also concentrated in the expiration phase. The filled circle dot indicates the grand—averaged respiration phase at button press. (c) A computed test statistics using original data (indicated by the blue vertical line) was significantly smaller than a chance level statistics obtained from phase shifted surrogate respiration data (indicated by a histogram; permutation p=0.0009), showing the timing of button presses in Experiment-2 is coupled with respiration phase.

Figure 3:
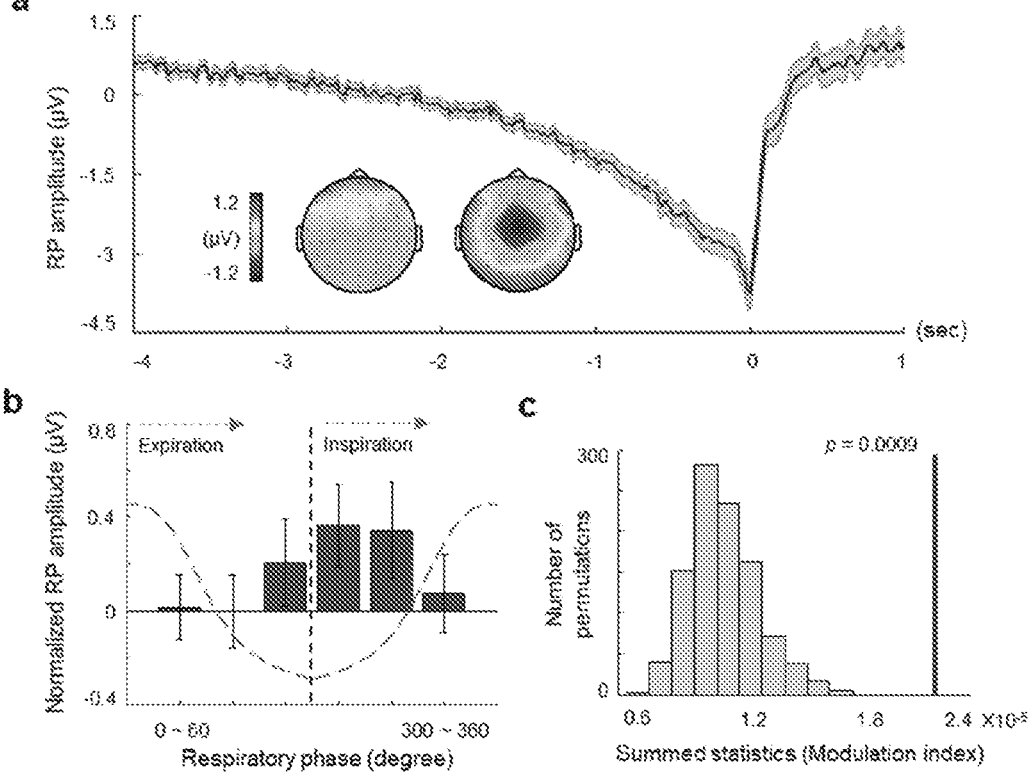

FIG. 3. Coupling between the respiratory phase and the Readiness potential (RP) amplitude. (a) RP waveform obtained from fronto-central electrodes (n=52). Gray shaded area represents the SEM. Inserted topographies were respectively obtained from the time windows (−4~−2 seconds; left) and (−2~0 seconds; right). (b) The amplitude of the RP as a function of six equally sized bins of the respiratory phase is shown. Error bars represent the SEM. (c) Histogram of the summed statistics (i.e., Modulation index; MI) obtained from surrogate respiration data whose phase is randomly shifted. The blue vertical line indicates the summed statistics from original respiration data. The result of a permutation test confirmed that the original MI is significantly larger than chance-level MIs obtained from surrogate respiration data (permutation p=0.0009).

Figure 4:
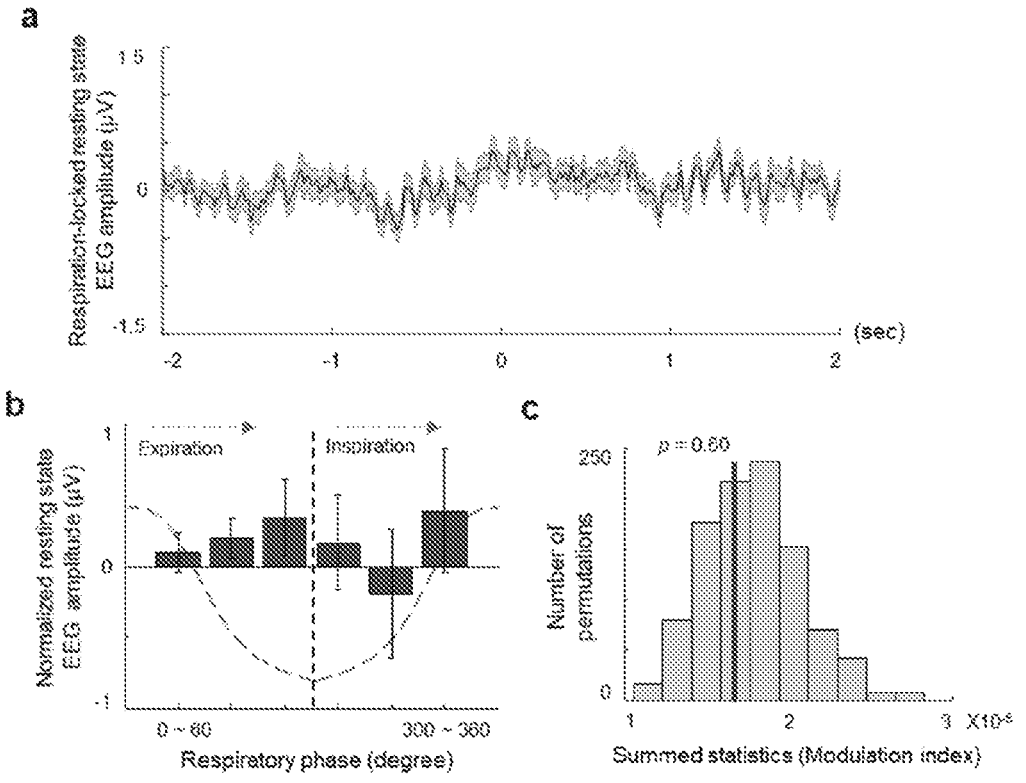

FIG. 4. Respiratory phase and resting state EEG amplitude. (a) Waveform of resting state EEG amplitude time-locked to the respiration (i.e., inspiration) peak obtained from fronto-central electrodes (n=50). Gray shaded area represents the SEM. (b) Resting state EEG amplitude as a function of six equally sized bins of respiratory phase. Error bars represent the SEM. (c) Histogram of the summed statistics (i.e., Modulation index) obtained from surrogate respiration data whose phase is randomly shifted. The blue vertical line indicates the summed statistics from original respiration data (permutation p=0.60).

Figure 5:
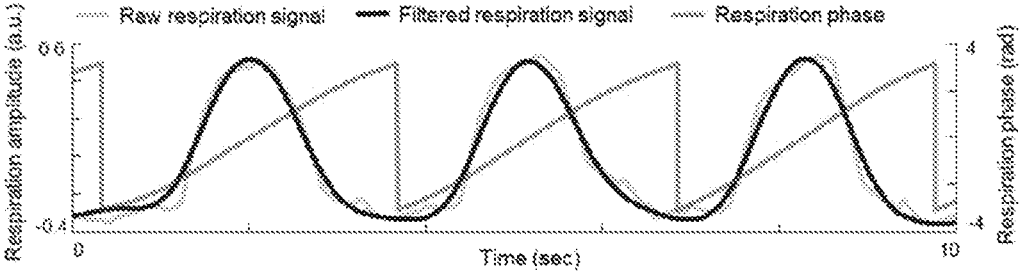

FIG. 5. Computation of respiration phase. Raw respiration signals were bandpass filtered between 0.2 and 0.8 Hz. Then the respiration phase was obtained using the Hilbert transform.

Figure 6:
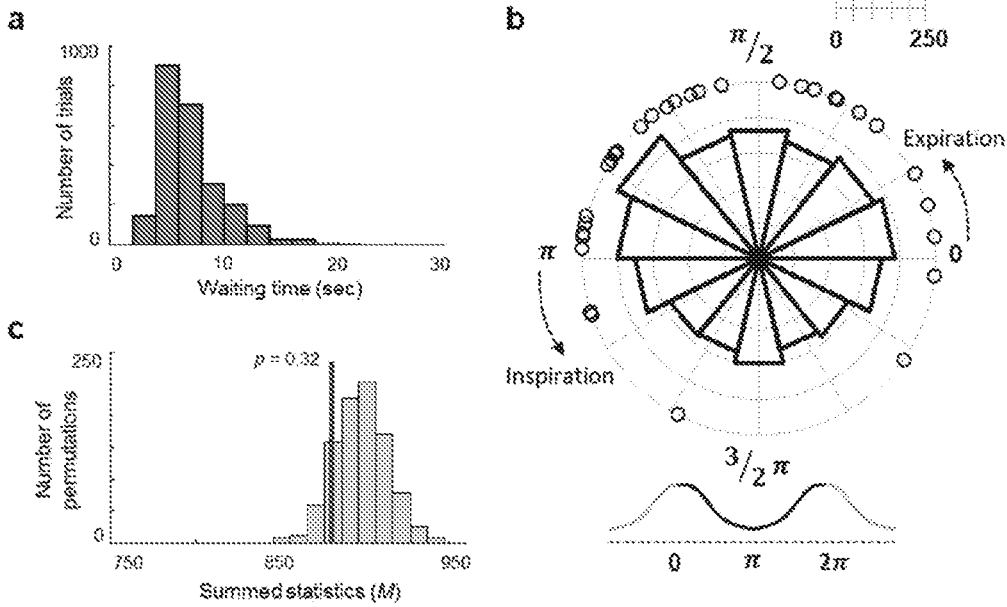

FIG. 6. The respiratory phase and the onset of externally-triggered button presses in Experiment-3. (a) Distribution of intervals from beginning of trial to the externally-triggered button presses (pooled across 32 participants). (b) Distribution of respiration phases with respect to the timing of externally-triggered button presses. The small black circle represents each participant's mean respiration phase at the button press. The polar histogram shows the distribution of all the externally-triggered button presses from 32 participants. (c) Histogram of the summed statistics (i.e., minimum number of data points that can be observed in half of the circle; Hodges-Ajne test) obtained from surrogate respiration data. The blue vertical line indicates the summed statistics from original respiration data. A computed test statistics using original data was not different from chance level statistics obtained from phase shifted surrogate respiration data (permutation p=0.32), confirming the timing of button press in Experiment-3 is not coupled with respiration phase.

Figure 7:
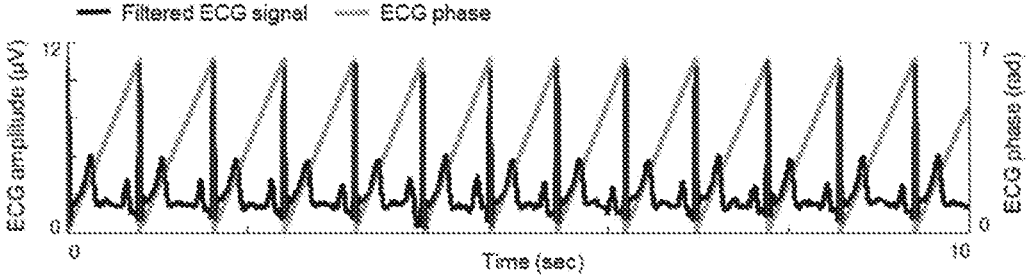

FIG. 7. Computation of cardiac phase. Heartbeat phase was computed using a method based on a peak detection algorithm.

Figure 8:
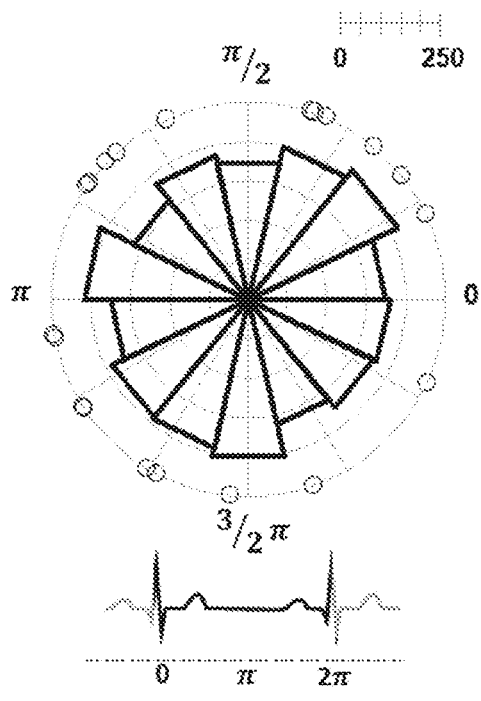

FIG. 8. Distribution of heartbeat phases at the timing of the voluntary action in Experiment-1. The small black circle represents each participant's mean heartbeat phase at the button press. No preferential phase emerged (Hodges-Ajne test, p=0.59, M=6). Polar histogram shows the distribution of all the button presses from 20 participants, which was uniformly distributed (p=0.80, M=1262).

Figure 9:
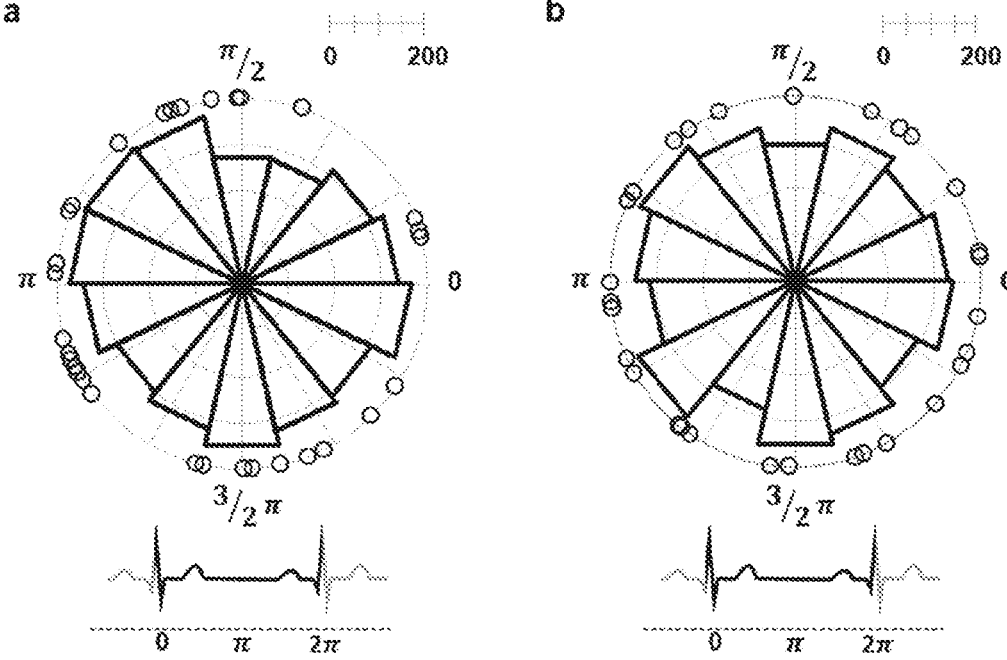
Figure 10:
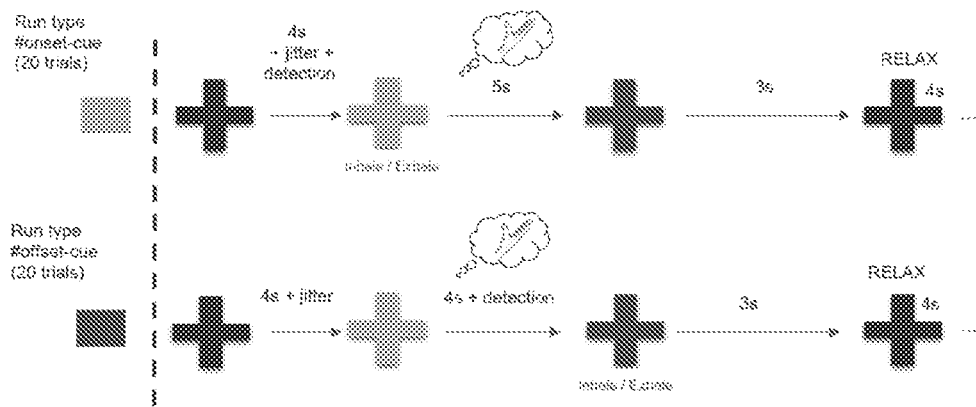
Figure 11:
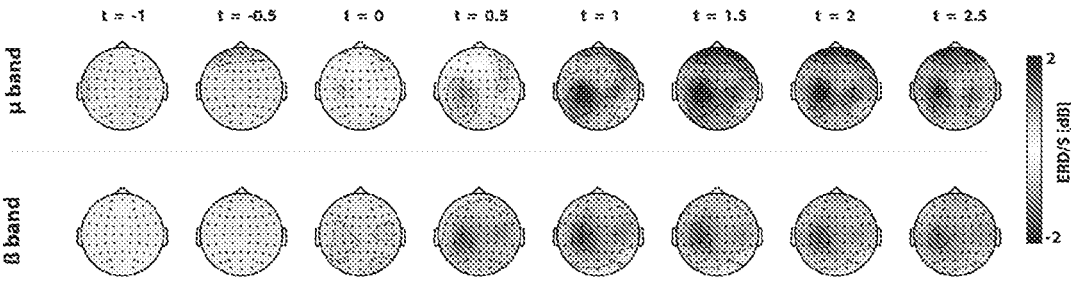
Figure 12:
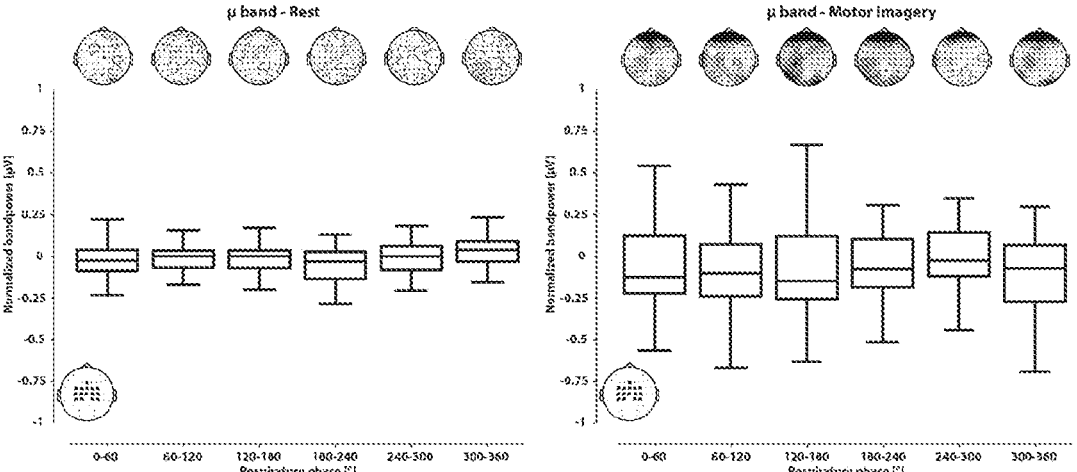
Figure 13:
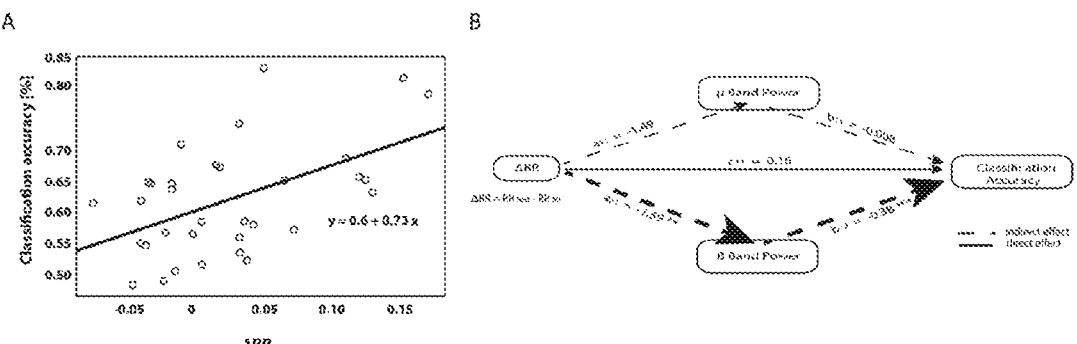
Figure 14:
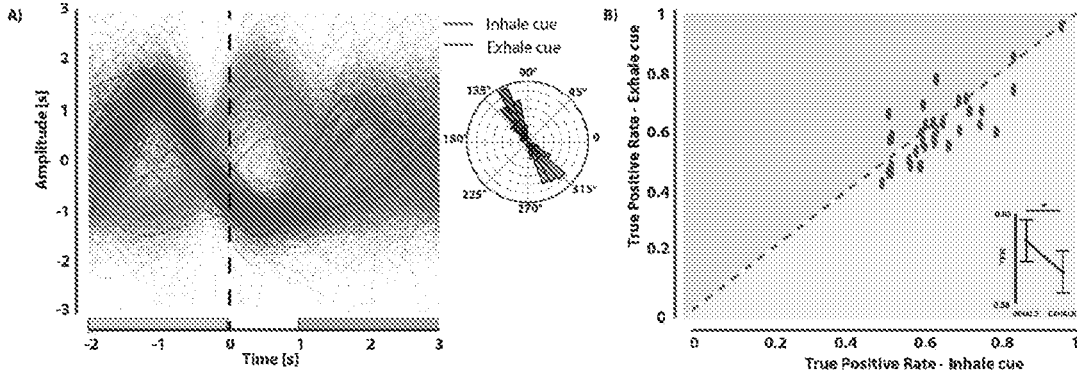
Figure 15:
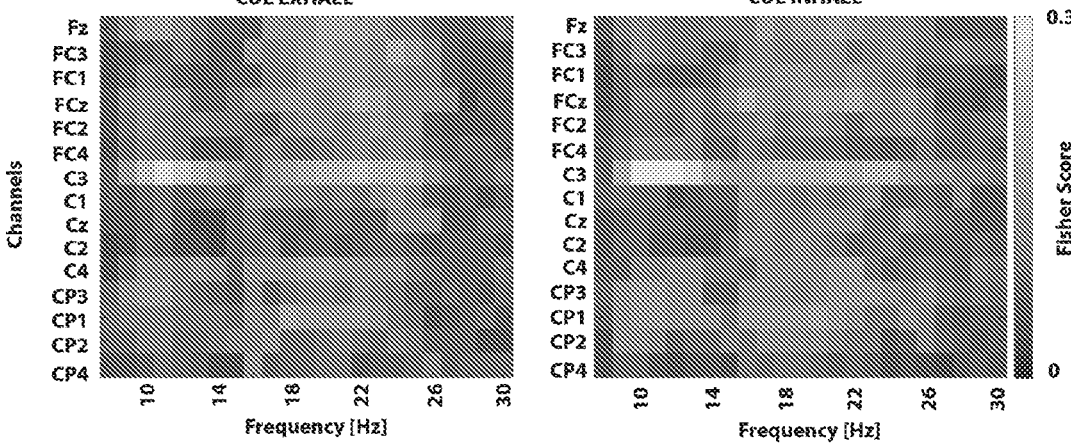

FIG. 9. Distribution of heartbeat phases at the timing of the button presses in Experiment-2 and 3. The small black circle represents each participant's mean heartbeat phase at the button press. No preferential phase emerged neither in the Libet task (a: Hodges-Ajne test, p=0.71, M=11) nor in the externally-triggered task (b: p=0.92, M=12). Polar histogram shows the distribution of all the button presses from 31 participants, which was uniformly distributed (a: p=0.24, M=1106; b: p=0.78, M=1125);

FIG. 10. MI task experimental protocol. The experiment was split into runs with different conditions (respiration-based onset cue or respiration based offset cue). In a run, the trials were split again into two conditions (inhalation-based cue or exhalation-based cue). A trial was organized into different blocks, first, the subject was asked to remain still and wait for the cue to turn green. Importantly, a jitter of 1 s was added to prevent the subject from anticipating the cue. Once the cue turned green (second cross from the left), the subject was instructed to perform the MI task and to stop MI when the cue turned red (third cross from the left). Once the cue turned red and that the subject stopped the MI task, she/he was asked to remain still during 3 s while continuing to fix the fixation cross. This was followed by a rest period of 4 s during which the participant could move or blink;

FIG. 11. Topographic maps of $\mu$ and $\beta$ bands averaged over all subjects. The power activity over time between [−1, 2.5] s are represented in this figure and is calculated over a 1 s window with an overlap of 0.5 s. The top layer shows the power changes in the $\mu$ band while the bottom layer shows the power changes in the $\beta$ band. Black color means a decrease in power;

FIG. 12. Respiratory phase coupling analysis for $\mu$ and $\beta$ band power activities. The band power was calculated for each channel for the 6 equally sized bins of the respiratory phase (x-axis). From the band power, a topographic map was represented for the $\mu$ and $\beta$ band power activities during a rest period [−3, −1] s and a MI period [1, 4] s. The average band power of 15 EEG channels of interest was calculated and represented as a boxplot. From the average band power, a modulation index was calculated and averaged over subjects. A permutation test (n=1000 permutations) was performed to see if the modulation index was significant. On the bottom right of each panel is shown the distribution of the modulation index when data were permuted (blue histogram—x-axis: modulation index value, y-axis: number of permutations). The vertical black line corresponds to the real modulation index averaged over subjects with the reported p-value corresponding to the number of permutations superior to the real modulation index;

FIG. 13. Performance on the randomized onset cue of MI. A) Feature mapping on randomized onset cue averaged over all subjects. Fisher scores are shown for the features (channels×frequencies). Higher values (i.e., white color) indicate highly informative features while black colors indicate fewer discriminant features. The scores were normalized for each subject using min-max scaling. B) Classification performances in function of respiratory rate changes between REST and MI period. Each point corresponds to the cross-validated accuracy of one subject in function of the averaged respiratory rate changes calculated between REST and MI period. A regression model was fitted to these data with x as the respiratory rate changes and y as the classification accuracy. The black line shows this model;

FIG. 14. Performance comparison between inhalation and exhalation onset of MI task. A) Detection of inhalation and exhalation for cuing MI task. The left panel shows the amplitude of respiratory signals. The line represents each subject averaged respiratory activity across trials (darker: exhale starting cue, lighter: inhale starting cue). The dashed vertical line represents the time when subjects are instructed to start their motor imagery. The white and black rectangles correspond to the time interval representing the REST and MI classes, respectively, during the decoding process. B) The scatter plot represents the average cross-validated decoding performances built on the inhale cue in function of the one obtained from the exhale cue. The decoding performances are assessed with the true positive rate of the MI class (i.e. the number of correct detections within MI class);

FIG. 15. Feature mapping between decoding trained on inhalation or exhalation onset of the MI task averaged over all subjects. Fisher scores are shown for the features (channels×frequencies). Higher values (i.e., white color) indicate highly informative features while black colors indicate fewer discriminant features. The scores were normalized for each subject using min-max scaling.

DETAILED DESCRIPTION OF THE INVENTION

The subject-matter described in the following will be clarified by means of a description of those aspects which are depicted in the drawings. It is, however, to be understood that the scope of protection of the invention is not limited to those aspects described in the following and depicted in the drawings; to the contrary, the scope of protection of the invention is defined by the claims. Moreover, it is to be understood that the specific conditions or parameters described and/or shown in the following are not limiting of the scope of protection of the invention, and that the terminology used herein is for the purpose of describing particular aspects by way of example only and is not intended to be limiting.

Unless otherwise defined, technical and scientific terms used herein have the same meaning as commonly understood by one of ordinary skill in the art to which this invention belongs. Further, unless otherwise required by the context, singular terms shall include pluralities and plural terms shall include the singular. The methods and techniques of the present disclosure are generally performed according to conventional methods well known in the art and as described in various general and more specific references that are cited and discussed throughout the present specification unless otherwise indicated. Further, for the sake of clarity, the use of the term "about" is herein intended to encompass a variation of +/−10% of a given value.

The following description will be better understood by means of the following definitions.

As used in the following and in the appended claims, the singular forms "a", "an" and "the" include plural referents unless the context clearly dictates otherwise. Also, the use of "or" means "and/or" unless stated otherwise. Similarly, "comprise", "comprises", "comprising", "include", "includes" and "including" are interchangeable and not intended to be limiting. It is to be further understood that where for the description of various embodiments use is made of the term "comprising", those skilled in the art will understand that in some specific instances, an embodiment can be alternatively described using language "consisting essentially of" or "consisting of."

In the frame of the present disclosure, the expression "operatively connected" and similar reflects a functional relationship between the different components of the device or a system among them, that is, the term means that the components are correlated in a way to perform a designated function. The "designated function" can change depending on the different components involved in the connection; for instance, the designated function of a computer device operatively connected with a system according to the invention is to e.g. operating said system in order to obtain and/or computing information retrievable from the analysis of neuroelectrical signals of a subject. A person skilled in the art would easily understand and figure out what are the designated functions of each and every component of the device or the system of the invention, as well as their correlations, on the basis of the present disclosure.

In neuroscience, the "readiness potential" (RP), also called the pre-motor potential, is a measure of the electrical activity in the motor cortex and supplementary motor area of the brain leading up to voluntary muscle movement. The RP is a manifestation of cortical activity contributing to the pre-motor planning of voluntary action, and appears to be generated and enhanced by intentional engagement of the subject prior to the execution of an action. On EEG tracings, the RP can be identified as a slow negative deflection preceding volitional movements, having an early component (peaking around −1000 ms before the action is performed) arising from Brodmann area 6, supplementary motor area (SMA), and lateral premotor cortex, and a late component (peaking around −300 ms before the action is performed) involving additionally primary motor cortex.

A "Brain-machine interface" or "BMI", also referred to as "Brain-computer interface" (BCI) is a biomedical signal processing field aiming at providing communication and control pathways between a subject's brain and an external device. BMIs are often directed at researching, mapping, assisting, augmenting or repairing human cognitive or sensory-motor functions. Using BMI, users such as patients with motor disabilities can control an external device and interact directly with their environment while bypassing the natural motor pathways. Using such technology combined with non-invasive neuroimaging techniques such as electroencephalogram (EEG), created a novel form of therapy which has shown great promise for e.g. stroke rehabilitation or tetraplegia in spinal cord injury. BMIs are usually based on a well know paradigm called Motor imagery (MI), which is the process where a person is asked to mentally rehearse a given motor activity without any over motor output. Two main types of MI can be distinguished. In visual imagery (VI), the person is asked to rehearse the movement and visualize it. In kinesthetic imagery (KI), the person is asked to rehearse the movement and focus on the bodily sensation associated with movement execution. Due to clearer patterns and better performance, the latter is usually preferred for BMIs even though it is more difficult to perform for naive subjects.

Following such paradigms, BMIs are usually trained by associating predefined triggered actions to the detection of specific changes in sensorimotor rhythms and locations that can be recorded using e.g. electroencephalogram (EEG). As an example, when performing hand MI, changes can be observed in contralateral motor areas over the hand motor regions of the brain and are usually referred to as Event-Related Desynchronization (ERD). ERD is a short-lasting attenuation of brain oscillations found in subjects during generation, observation, and imagery of movement, typically considered to reflect cortical motor activity and action-perception coupling. Such patterns correspond to a decrease of power generally observed in $\mu$ [8-12] Hz and $\beta$ [13-30] Hz bands.

As used herein, a "respiratory signal" relates to any quantifiable data obtainable from the analysis of breathing (or ventilation, including artificial ventilation) parameters of a subject. A respiratory signal can be obtained through one or more tools, alone or in combination, that are configured to quantify, analyse, measure or otherwise retrieve breathing parameters such as blood oxygenation level, breathe rate, changes in blood volume, changes in thoracic/abdominal circumference, nasal/oral air flows; suitable devices or systems comprise a photoplethysmogram, respiration belts, electrocardiograms, spirometer, video recording and others.

The term "subject" as used herein refers to animals, preferably mammals, more particularly humans.

As used herein, "treatment" and "treating" and the like generally mean obtaining a desired physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it for example based on familial history, overweight status or age; (b) inhibiting the disease, i.e., arresting its development; or relieving the disease, i.e., causing regression of the disease and/or its symptoms or conditions such as improvement or remediation of damage. The term "diagnosis", "diagnostic" and the like refers to identifying the presence or nature of a pathological condition in a subject.

The main object of the present invention relates to a method for determining the intention of performing a voluntary action in a subject, comprising the steps of:

Obtaining neuroelectrical signals from said subject, said neuroelectrical signals comprising one of a Readiness Potential (RP) amplitude signal and $\mu$- and/or $\beta$-Event-Related Desynchronization ($\mu$-ERDs/$\beta$-ERDs) power measurement;

Obtaining respiratory signals from said subject, said respiratory signals comprising an expiration phase signal;

Comparing said RP amplitude signal and/or said $\mu$-ERDs/$\beta$-ERDs power measurement with said respiratory signals within a time-window, thereby obtaining a time-based correlation between said RP amplitude, and/or said $\mu$-ERDs/$\beta$-ERDs power measurement, and said respiratory signals; and Determining the intention of performing a voluntary action based on the comparison step.

In one embodiment, a lower RP amplitude signal in correspondence of an expiration phase of the respiratory signals is indicative of the intention of performing a voluntary action.

In additional or alternative embodiment, a $\mu$-ERDs/$\beta$-ERDs power decrease is indicative of the intention of performing a voluntary action.

As previously anticipated, the present method can be useful for studying and detailing the behavioural and brain mechanisms regulating the coupling of interoceptive respiratory signals with electrical neuronal signatures typical of voluntary action, thereby establishing novel paradigms among physiological markers and opening new perspectives in the understanding of body-brain relationships; as a way of example, the present method can unveil, through the simple study and modulation of easily accessible breathing parameters, novel brain areas involved in the origination of voluntary actions, of particular importance when such areas are impacted in patients suffering for instance from a muscular disease (including neurodegenerative muscular disease), a neurological disease, a respiratory disease and/or a psychiatric/psychotic disorder.

As used herein, the term "psychiatric" means related to or pertaining to psychiatry. Psychiatry is a field of medicine focused specifically on brain and mind, aiming to study, diagnose, prevent and treat mental disorders in humans, which include various affective, behavioural, cognitive and perceptual abnormalities.

The method of the present invention can be used for the treatment, diagnosis and/or prevention of at least some aspects of a psychiatric condition in a subject in need thereof.

For example, the implementation of the method of the invention could be used to exploit the data obtainable by respiratory signals (easily accessible and measurable physiological markers) for the functional analysis of associated brain areas involved in exemplary conditions like obsessive-compulsive disorder (OCD) or Tourette's syndrome, in which a strong involuntary movement component is present, or other conditions as Parkinson's disease or Chronic Obstructive Pulmonary Disease. In this context, the patients can be systematically "mapped" with regards to their action/breathing correlations, such as the "coupling strength" between respiratory phase parameters and the RP amplitude and/or μ-ERDs/β-ERDs power measurement, and said relationships could become a diagnostic marker, and said relationships could also be translated and used in rehabilitation feedback trainings. In a possible rehabilitation scenario, patients suffering from muscular disease and/or a neurological disorder, as a way of example, could be envisaged undergoing a novel kind of "movement-and-breathing therapy" in order to alleviate e.g. motor symptoms and/or achieve prophylactic effects.

Generally speaking, neuroelectrical signals useful in the frame of the present method comprise any electrical activity of the brain that can be monitored with any type of electrophysiological monitoring method. Examples of suitable monitoring methods are EEG, electrocorticography (ECoG), magnetoencephalography (MEG), event-related potentials (ERPs) detecting techniques and the like. In the implementation of the method of the invention, said neuroelectrical signals may preferably comprise EEG-derived signals. The use of EEG provides several advantages compared to other techniques such as a very high temporal resolution, easy availability and application of EEG scalp electrodes, detection of the RP with only few scalp electrodes, does not need a specially shielded room, i, does not aggravate claustrophobia and can be conducted with relatively simple paradigms, to cite a few.

On the other hand, respiratory signals suitable in the frame of the method of the invention are preferably obtained by measuring, during breathing, at least one of changes in thoracic/abdominal circumference, nasal air flows and electrical potential on the body surface.

The method exploits in some embodiments a time-based correlation between an RP amplitude and/or a change, such as a decrease, of μ-ERDs/β-ERDs power, and the measured respiratory signals obtained by superposing said RP amplitude signal, and/or said μ-ERDs/β-ERDs power, with said respiratory signals in real time. In embodiments, the RP amplitude and/or said μ-ERDs/β-ERDs power is/are averaged depending on respiration phase, and then correlation between them is quantified. For instance, the RP amplitude can be averaged depending on a series of respiration phase "portions", such as for instance six equally sized respiration phase bins.

In some embodiments of the invention, the method can be adapted to further comprise additional, optional steps of imaging, measuring or otherwise determining the activity of the subject's brain while the subject is undergoing the procedures related to the method of the invention. Said steps can be performed for example through a functional magnetic resonance imaging (fMRI) system operably connected with a system of the invention, detailed later on, in order to obtain cerebral "maps" of brain activity, even in real time.

As anticipated, the present invention contemplates also a system for implementing the method according to the invention, said system comprising:

a device configured to obtain neuroelectrical signals from a subject, said neuroelectrical signals comprising a Readiness Potential (RP) amplitude signal operatively coupled with a device configured to obtain respiratory signals from the same subject, said respiratory signals comprising an expiration phase signal. Generally speaking, said system may comprise any electrophysiological monitoring device capable of detecting electrical activity of the brain operatively coupled with any device capable of providing breathing parameters of a subject. In some preferred embodiments, a device configured to obtain neuroelectrical signals from a subject comprises an EEG device. In embodiments of the invention, a device configured to obtain respiratory signals from a subject can be selected from a non-limiting list of devices including a respiratory belt, a nasal/oral spirometer, a plurality of electrodes and/or video or voice recording means.

Advantageously, a system according to the invention can further comprise an operatively coupled computer device comprising a computer program comprising instructions to implement the method of the invention. The computer device can operate, such as modulate the operation of, any one or all the components of the system of the invention, including means for obtaining neuroelectrical signals from a subject and/or means for obtaining respiratory signals from said subject, said respiratory signals comprising an expiration phase signal.

The computer device can be any suitable device such as computers, smartphones, tablets, voice-activated devices (i.e. smart speakers/voice assistants) and the like, and comprises a data processing system including a processor configured to perform the computer-implemented method of the invention. The data processing system is preferably operatively connected to the system's elements so to interconnect them and operate the entire apparatus in a coherent fashion.

The data processing system may comprise a computer-readable data carrier storing software that provides functionality when executed by the processor as well as an operating system that provides operating system functionality for the entire apparatus. For "computer-readable data carrier" or "computer-readable medium" is herein meant any available medium that can be accessed by a processor and may include both a volatile and non-volatile medium, a removable and non-removable medium, a communication medium, and a storage medium. A communication medium may include computer readable instructions, data structures, program modules or other data in a modulated data signal such as a carrier wave or other transport mechanism, and may include any other form of an information delivery medium known in the art. A storage medium may include RAM, flash memory, ROM, erasable programmable read-only memory ("EPROM"), electrically erasable programmable read-only memory ("EEPROM"), registers, hard disk, a removable disk, a compact disk read-only memory ("CD-ROM"), or any other form of a storage medium known in the art. The computer device can include a communication device, such as a network interface card, to provide mobile wireless communication, such as Bluetooth, infrared, radio, Wi-Fi, cellular network, or other next-generation wireless-data network communication. In other aspects, communication device can include a wired network connection, such as an Ethernet connection or a modem.

Preferably, the computer device comprises instructions to compare and correlate RP amplitude signals, and/or μ-ERDs/β-ERDs power measurement, with respiratory signals within a time-window, thereby obtaining a time-based correlation between said RP amplitude, and/or μ-ERDs/β-ERDs power measurement, and said respiratory signals. The recorded data can be compared, depending on the needs and circumstances, with reference data of neuroelectrical signals, respiratory signals and/or correlated RP amplitude signals/μ-ERDs/β-ERDs power measurement with respiratory signals, provided in e.g. cloud or stored databases. All raw and/or correlation data can possibly be graphically or numerically shown on associated display means. Advantageously, the use of the respiration phase data/parameters can be used to change the prior of an intention-detecting classifier based on the RP potential and/or μ-ERDs/β-ERDs power. This has the advantage of increasing the accuracy of the classifier (as the likelihood to perform an action may not be equally distributed throughout the respiration phases). In other words, the information obtainable by associating and correlating data regarding breathing parameters with RP amplitude data/μ-ERDs/β-ERDs power measurement data allows to optimize and perfect an intention-detecting algorithm with regards to an algorithm based only on neuroelectrical signals.

Advantageously, and within the frame of the invention, the computer device can further comprise instructions to actuate an external device based on a time-based correlation between an RP amplitude, and/or μ-ERDs/β-ERDs power measurement, and respiratory signals. In this context, the system of the invention can be considered as a so-called "Human-Machine Interface" (or "HMI") or "Brain Machine Interface" ("BMI") that may have several, diverse applications and significant impact in e.g. robotics and rehabilitation/treatment of numerous diseases. For instance, the system and the method of the invention can be used for operating robotic devices, exoskeletons, daily-life machines or transport apparatuses such as cars or wheelchairs by computing respiratory signals in correlation with RP amplitude, neuroelectrical signals. In patients with severe movement disorders (i.e. tetraplegia) suffering from neurological, neurodegenerative and/or neuromuscular diseases, the system and the method of the invention could be exploited in order to determine whether a subject intends to voluntarily perform an action (such as a movement), and operating accordingly a coupled external device. In a possible approach, patients suffering from certain diseases can be trained to trigger or modulate a neuroelectrical signal, and particularly an RP amplitude signal, by controlled "breathing protocols". Accordingly, information about the breathing cycle and breathing performance and further data extrapolation could be integrated in the design of an HMI/BMI, and breathing-movement paradigms could be instructed or taught to a subject in order to foster MI correlates and hence build more accurate HMI/BMI.

Additionally, by analysing and gathering data regarding the identified time-based correlation, such as the coupling strength, of time-based correlation between neuroelectrical signals such as RP amplitudes and respiratory signals, novel and more powerful artificial intelligence may be developed, for instance by training machine learning algorithms as to how better operate devices as the human brain operates, or imagine to operate, its body upon volition.

The following non-limiting examples are provided herein below to better clarify the inventive concept of the present invention.

EXAMPLES

Respiratory Phase is Coupled with Voluntary Action

In Experiment-1, participants performed the Kornhuber task (3) and were instructed to press a button on a keypad in a self-initiated manner roughly every 8 to 12 seconds. Participants were explicitly instructed to not use any strategies such as counting numbers (e.g., seconds) and to try to use irregular intervals to maximize spontaneity of the task, as typically done in this voluntary action task (3, 21). When pooled across 20 participants, the distribution of intervals between button presses (i.e., waiting time) showed a rightward skewed shape (FIG. 1a) in-line with previous voluntary action studies (1, 9). The interval between button presses was on average 11.20±2.30 sec (mean±SD), and the standard deviation of these intervals was on average 3.26±1.70 sec, indicating that participants successfully performed the Kornhuber task.

Figure 1:
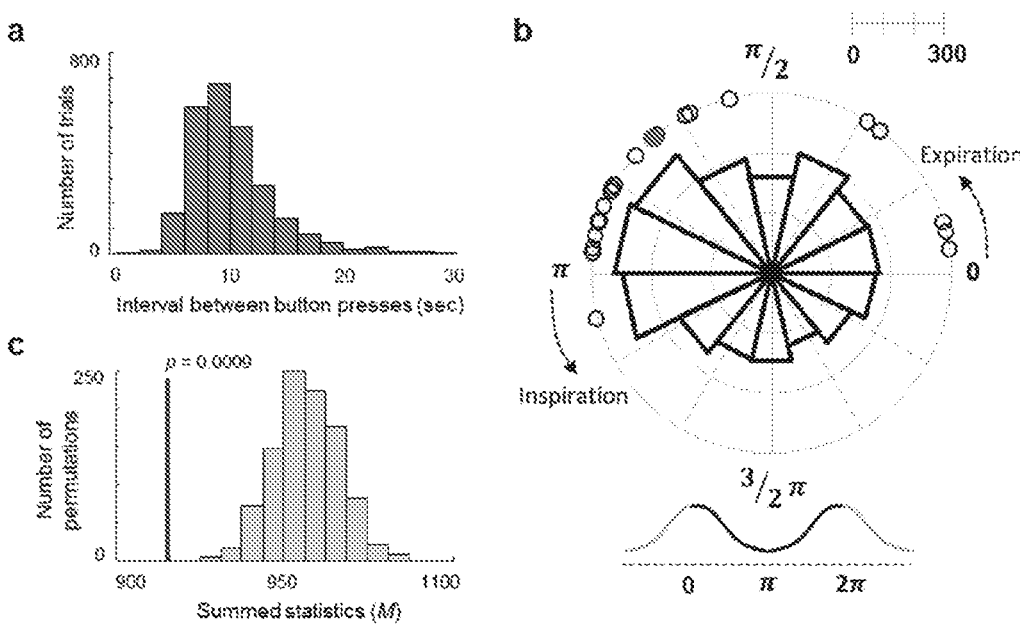
FIG. 1. Coupling between voluntary action and respiratory phase during the Kornhuber task in Experiment-1. (a) Distribution of intervals between button presses (pooled across 20 participants) showed the typical response distribution. (b) Distribution of respiration phases with respect to the timing of voluntary action onset. Empty black circles represent each participant's mean respiration phase at button press. Participants initiated voluntary actions more frequently during the late phase of expiration. The polar histogram shows the distribution of all the button presses from 20 participants, which was also concentrated in the late phase of expiration. The filled circle dot indicates the grand-averaged respiration phase at button press.

The first test consisted to check whether the onset of voluntary movement is associated with spontaneous breathing signals. For this, the phase of respiration was computed at the onset of button presses, using the Hilbert transform (FIG. 5). It has been found that participants pressed the button more frequently during the expiration phase, in particular during the latest phase of expiration, just prior to inspiration onset (FIG. 1b, c; permutation test, p=0.0009). The mean respiration phase at the moment of button press was observed for 19 out of 20 participants during the expiration phase, that is between 0 and π (see open black circles in FIG. 1b). After the experiment was terminated, we asked all participants whether they had been aware of any relationship between their breathing or heartbeat and the button presses (Q1), and whether they had used their breathing or heartbeat to press the button (Q2). Among 20 participants, 18 responded 'No' to Q1/Q2, suggesting that the group of participants was unaware of the observed link between voluntary movement and respiration.

In two further experiments, it has been aimed to 1) replicate the breathing-voluntary action coupling in a separate group of new participants (N=32) using a different voluntary action task, the classical Libet task (5) (Experiment-2), and to 2) test whether the observed coupling effect is specific to voluntary action or whether it extends to non-voluntary action (Experiment-3). During the Libet task (Experiment-2), participants were asked to press the button at any time they wanted to, while they were asked to look at a clock face with a rotating filled circle dot. Participants estimated the time when they first felt the intention to press the button (i.e., W-time). The waiting time for the button press was on average 6.67±1.52 sec (FIG. 2a), and the standard deviation of waiting time was on average 2.20±0.97 sec. W-time was on average −0.26±0.17 sec. These behavioral results of waiting time and W-time are comparable with previous studies using the Libet task (1, 9).

Importantly, participants pressed the response button more frequently during the expiration phase (FIG. 2b, c; permutation test, p=0.0009), replicating the results from Experiment-1. The mean respiration phase at the moment of button press was observed for 30 out of the new 32 participants during the expiration phase (see open black circles in FIG. 2b). Upon completion of the study, all participants were asked whether they had been aware of any relationship between their breathing or heartbeat and the button presses (Q1), and whether they had used their breathing or heartbeat to press the button (Q2). From a total of 32 participants, 31 responded 'No' to Q1/Q2 (only one participant responded 'yes' to (Q1), but not (Q2)).

Respiratory Phase is not Coupled with Non-Voluntary Action

During the externally-triggered action task (Experiment-3), participants were asked to press the response button as soon as they perceived a green dot at the center of the clock face. The interval from beginning of the clock rotation to the button presses was on average 7.03±1.56 sec (FIG. 6a) and the standard deviation of intervals was on average 1.98±0.85 sec. A permutation test confirmed that during the externally-triggered action task, participants' button presses were not coupled with the breathing phase (FIG. 6b, c; permutation test, p=0.32). These results show that the reported coupling between the respiration phase and the movement onset is specifically observed for voluntary actions, but not during externally-triggered actions in an otherwise identical experimental setup.

Cardiac Phase is not Associated with Voluntary Action

It was next checked whether the phase of cardiac signal is associated with voluntary movement onset. For this analysis, the phase of the ECG signal was calculated based on a peak detection algorithm (FIG. 7) (25), rather than Hilbert transform (see Methods). In Experiment-1, the distribution of cardiac phases at the timing of button press was not non-uniform (FIG. 8; Hodges-Ajne test for all the button presses across 20 participants, p=0.80, M=1262; Hodges-Ajne test for mean values across 20 participants, p=0.59, M=6). There was no significant association between the cardiac phase and button press in Experiment-2 (Libet task, FIG. 9a; Hodges-Ajne test for all the button presses across 31 participants, p=0.24, M=1106; Hodges-Ajne test for mean values across 31 participants, p=0.71, M=11) nor in Experiment-3 (externally-triggered action task, FIG. 9b; Hodges-Ajne test for all the button presses across 31 participants, p=0.78, M=1125; Hodges-Ajne test for mean values across 31 participants, p=0.92, M=12). These results indicate participants' button presses were not associated with the cardiac phase.

Taken together, the behavioral results show that the spontaneous breathing phase, but not the cardiac phase, is coupled with the onset of voluntary action, as tested in two classical voluntary motor tasks, and this respiration-action coupling is absent during externally trigged actions. The questionnaire data further indicate that the participants were not aware of this coupling between respiration and their voluntary actions.

Coupling Between Respiratory Phase and RP Amplitude

Next, the idea that respiration signals could affect the RP was tested, based on the observed behavioral coupling between respiration and voluntary action. For this, EEG-respiration data from Experiment-1 and Experiment-2 were combined, because 1) these two classical paradigms (Kornhuber task, Libet task) have been most commonly used in RP research, because 2) similar breathing-action were observed coupling in both voluntary action tasks, and because 3) it was thereby wanted to increase statistical power for single trial RP analysis (26). Typical RPs were first identified by averaging EEG signals preceding the onset of voluntary finger movements (FIG. 3a). In accordance with previous findings, RPs were observed in central and fronto-central regions beginning around 2 seconds before the voluntary action onset.

It was next tested directly whether the RP amplitude is associated with the phase of concurrently measured respiration signals. In brief, the mean RP amplitude was computed in each single trial depending on six equally sized bins of the respiration phase. Then, to determine the statistical significance of coupling between respiration phase and RP amplitude, a Modulation index (MI) was computed in each participant (see Methods) (15, 27, 28). The results show that the RP amplitude was smaller during the expiration periods compared to the inspiration periods (see FIG. 3b). Permutation test confirmed the significant phase-amplitude coupling between respiration and RP by showing that the MI computed using the original data is significantly larger than surrogate MIs obtained from phase shifted respiration signals (FIG. 3c; permutation p=0.0009).

Resting State EEG is not Modulated by Respiratory Phase

In a final EEG analysis, it was investigated whether the phase of respiration is related to the modulation of resting state EEG amplitude to exclude the possibility that the observed coupling between the RP amplitude and respiration phase might reflect mere artefactual influence of respiration on EEG signals. For that the resting state EEG signal that was time-locked to the respiration peak (i.e., inspiration) was computed, from the same electrodes that were used for RP computation, and then computed the MI between the resting state EEG amplitude and the respiration phase (FIG. 4a, b). Analysis (permutation test) showed that the computed MI using the original data is not different from the chance-level MI obtained from phase shifted respiration data (FIG. 4c; p=0.60).

This shows that the resting state EEG amplitude does not depend on the respiration phase, indicating that the coupling between respiration signals and the RP amplitude is not related to artefactual influence of the respiration signal on EEG activity at rest.

Methods

Participants In Experiment-1, 20 participants (10 female; 20 right-handed; mean age: 26±1.3 years) took part in the study. In Experiment-2 and 3, 34 participants (15 female; 31 right-handed; mean age: 26.5±5.1 years) conducted the experiments. Two participants were excluded from analysis due to the excessive movement artifacts contaminating more than 50% of both respiration and EEG signals. In addition, 1 participant was excluded from cardiac phase analysis due to noisy ECG signals, and 2 participants were excluded from resting state data analysis due to missing trigger signals. All participants reported no history of neurological or psychiatric disorders nor cardiovascular diseases.

Paradigm In Experiment-1, participants performed the Kornhuber task (3, 21). An experimental session consisted of 3 blocks of 8 minutes. Participants were instructed to press a button on a keypad voluntarily using their right index finger. To produce one voluntary movement per roughly 3 respiration cycles, participants were asked to press the button every 8 to 12 seconds. Importantly, participants were asked 1) not to count any numbers (e.g., seconds) to estimate the time, 2) to avoid making regular or rhythmic button presses (3, 9) to maximize the spontaneity of the task. Before the real recordings, participants conducted a short training session (~1 minute) and the experimenter gave feedback on the interval and regularity of their button presses, so that participants could adjust them. Throughout the experiment, participants were acoustically isolated with continuous white noise via insert earphones and closed eyes. The first trials in each block were excluded from the analysis (<3%), as participants often involuntarily pressed the key at the beginning of white noise. Inclusion of such trials did not affect the results. At the end of Experiment-1, resting state EEG data (for 3 minutes) were acquired while participants had their eyes closed.

An independent group of participants conducted Experiment-2 and 3. In Experiment-2, participants performed the Libet task (5). A trial was initiated when a red dot appeared at a random location of the clock face (radius: 2° of visual angle). The red dot then rotated at 2560 ms per cycle. Participants were instructed to wait for at least one full rotation and after that to press the button at any time they wanted by using their right index finger.

In-line with previous studies, the participants were asked to avoid 1) pre-planning the location of the dot for the button press, and 2) using same intervals across trials (for previous work and instructions see 5, 9, 37). After the participant pressed the button, the red dot disappeared immediately. After 4 seconds, the red dot reappeared at the same location, and the participants indicated the clock position which they first felt the conscious urge (or intention) to press the button using the key pad. After a random inter-trial interval (i.e., 4 to 8 seconds), the next trial began.

In the externally-triggered task of Experiment-3, participants were asked to press the button as fast and accurately as possible after detecting a green dot which appeared for 200 ms at the fixation point while the red dot was rotating (i.e., as in the Libet task). Once the button was pressed the red dot disappeared immediately. After a random inter-trial interval (i.e., 4 to 8 seconds), the next trial began. The interval of the green dot appearance was based on each participant's performance during the previous Libet experiment. Participants performed 3 blocks (i.e., 75 trials in total; one participant conducted 90 trials) for Experiment-2 and for Experiment-3. In order to collect the individual interval data for the green dot appearance in Experiment-3, the experiment always began with the Libet task, while the remaining 5 blocks were pseudo randomized.

After participants had completed Experiment-2 and 3, EEG resting state data for 5 minutes were acquired while participants were asked to fixate the center of the screen.

Respiration recording and analysis Continuous respiration signal was collected using a respiration belt (Biopac MP36, Biopac System Inc) at a sampling rate of 2000 Hz. Preprocessing and averaging were conducted using the Fieldtrip toolbox (38). To determine the instantaneous respiration phase at the timing of button presses, the continuous respiration signal between 0.2 and 0.8 Hz was first bandpass filtered, and then applied Hilbert transform (FIG. 5). Inspiration peaks were detected by correlating respiration signal with a template defined on a subject-by-subject basis (10).

EEG recording and analyses EEG signals were collected using a 64-channel active electrode EEG system (ActiveTwo system, Biosemi) at a sampling rate of 2048 Hz and online low-pass filtered at 400 Hz. Continuous EEG data were down-sampled to 512 Hz and offline filtered between 0.1 and 40 Hz, following a recent observation that applying a high pass filtering at 0.1 Hz effectively reduces infra slow oscillations when computing slow brain potentials such as the RP (39). EEG data were re-referenced to a common average reference, as in a recent RP study (40).

RP was computed on EEG signals locked to the onset of the button press. After epoching (−4 to 1 sec regarding the movement onset), trials showing excessive noise (i.e., >3 SD) were excluded from further analysis. After artifact correction, 118±24 (in Experiment-1) and 68±4 epochs (in Experiment-2) were averaged in each subject to compute the RP. Baseline correction was not applied (9). RPs are typically observed in fronto-central electrodes (3, 7, 9, 40). To maximize the signal-to-noise ratio, RP results from electrodes that showed the highest RP amplitude among fronto-central electrodes (i.e., Cz, FCz, Fz, AFz) are reported, defined on a subject-by-subject basis.

ECG recording and analysis ECG signals were simultaneously recorded using the abovementioned EEG amplifier and also the same preprocessing was applied to both EEG and ECG signals as described above. Bipolar ECG electrodes were placed over the right shoulder and the bottom of the left side of the abdomen. To compute the phase of ECG signal at the button press, a method based on a peak detection algorithm was applied, as the Hilbert transform cannot be applied to the ECG signal which does not have oscillatory shape. For that, R-peaks were detected by correlating the ECG signal with a template QRS complex defined on a subject-by-subject basis (10). Then the phase of the ECG signal was calculated (FIG. 7) using the following formula:

$$\varphi(t)=2\pi((t-ta)/(tb-ta))$$

where ta and tb are the timings of two successive peaks surrounding the current time sample (25).

Statistical test of breathing-voluntary action coupling The significance of the relationship between the timing of button presses and the phase of respiration signals was tested using a permutation-based two-step process. For each participants, the Hodges-Ajne test (or Omnibus test) was first applied, which assesses the uniformity of circular data such as a phase distribution without assumptions on the distribution of the data (41), as implemented in the Circular Statistics Toolbox (42). The Hodges-Ajne test results in a test statistic (i.e., M) defined as the minimum number of data points that can be observed in half of the circle. The null hypothesis of uniform distribution is rejected when the test statistic is smaller than the expected numbers (41). Importantly, considering that the expiration duration is longer than inspiration one (see FIG. 5), it is expected that even completely random events that are not associated with breathing cycle will be more likely observed during the expiration phase. Thus, as a second step, the computed original statistic (i.e., sum of M across all participants) was compared to the null distribution of surrogate M values that are obtained from phase shifted respiration data. For that the phase of respiration signals was cut into two segments with a random amount, and the order was swapped in each block and subjects (27). 1000 surrogate M values were created which defined the chance-level coupling between the respiration phase and button presses. Then, a two-sided Monte Carlo p-value was obtained.

Modulation index between RP amplitude and respiratory phase For assessing the coupling between the respiratory phase and the RP amplitude, the RP amplitude was first computed and respiration phase in each single trial in a −4 to 0 second time-window (i.e., around 1 respiratory cycle) regarding the onset of the button press. Then, the RP amplitude was averaged depending on six equally sized respiration phase bins that spanned the 0 to $2\pi$ interval. Trials that did not result in six mean RP amplitudes across six respiration phase bins (<2% of total trials) were excluded from further analysis. Sorted RP amplitudes in each breathing phase bins were normalized (i.e., dividing by the sum of all RP amplitudes in each trial; see FIG. 3). The degree of coupling between the sorted RP amplitude and respiration phase was quantified by computing the Modulation index (MI) (15, 28), which quantifies how much a given distribution of amplitudes across phase bins deviates from a uniform distribution, using mean RP amplitudes across single trials in each six respiration phase bin for each subject. Stronger phase-amplitude coupling (i.e., more deviation from uniform distribution) results in the higher MI values.

MI significance was tested using a permutation test for which grand-averaged MI across all participants was first computed, using the original EEG-respiration data. Then the original grand-averaged MI was compared to the null distribution of surrogate MI values that the phase-amplitude association was disrupted by randomly shifting the respiration phase data as explained above. 1000 surrogate MI values were created which defines the chance-level coupling between the RP amplitude and respiration phase. Finally, a two-sided Monte Carlo p-value was obtained.

To compute the coupling between respiration phase and resting state EEG amplitude, EEG data was epoched in −2 to 2 second time-windows around the inspiration peak (see FIG. 4). The same procedure was then applied between the resting state EEG amplitude and the concurrently measured respiration phase, as explained above.

Discussion

The first major observation of the present study is that the breathing pattern of the participants was systematically coupled with the onset of their voluntary movements, despite the fact that the participants were entirely free to choose the movement onset within the experimental constraints. These results were obtained using the two most frequently used voluntary action paradigms: the Kornhuber (Experiment-1) and the Libet task (Experiment-2) and were obtained in two different subject samples. It has been pointed out that, whereas the Kornhuber paradigm may involve additional cognitive task-related components such as interval estimation, this is not the case during the Libet task (9), confirming the coupling between respiration and voluntary action. In addition, the inventors showed that respiration phase was not coupled with involuntary action (i.e., externally-triggered action) in Experiment-3. Taken together, the findings from three experiments show that respiration phase is associated with voluntary action, but not interval estimation or externally-triggered actions.

Whereas previous work has demonstrated that interoceptive processing (including respiration) influences diverse sensory processes (10, 11, 24), the findings based on the present invention provide experimental evidence that interoceptive processing is associated with voluntary action control in humans.

Breathing is inevitably linked to orofacial movements such as speaking and swallowing, due to their shared anatomical structures (e.g., the pharynx and larynx) for airflow control. The results based on the present invention, showing the relationship between breathing and action control, go beyond these homeostatic controls and reflexes, revealing that the respiratory system affects voluntary action, a higher-level motor control function that has been associated with free will and self-consciousness in humans.

It has further been observed that the amplitude of the RP, which is the neural hallmark of voluntary action, is coupled with the phase of simultaneously recorded respiration signals. The MI between the respiration phase and the RP amplitude was computed, following previous studies measuring phase-amplitude coupling between two electrophysiological signals (15, 27, 28), and observed smaller RP amplitude during the expiration compared to the inspiration period. It is argued that this finding is in accordance with the recent proposal that the RP reflects fluctuations of background neuronal activity (4, 8, 9), rather than specific neural events associated with the motor preparation for the button press. Applying evidence accumulation modeling to the voluntary action paradigm, recent work showed that the timing of voluntary action and the associated RP can be explained by the accumulation of stochastic fluctuations in neural activity which eventually reaches a decision threshold (4, 9), and it has been suggested that the RP might reflect 'ebb and flow of background neuronal noise' (8). The present data are of relevance for the origin of such stochastic neuronal fluctuations that eventually generate the RP.

Based on the present data it is argued that such fluctuations of background neuronal activity are neither 'noise' nor 'spontaneous', as they are, at least partly, accounted for by respiration signals. This interpretation is further strengthened by recent findings that interoceptive processing, in particular respiratory signal processing, is an important source of 'spontaneous' ongoing neural activity (15, 16). Taken together, it is proposed that the neuronal fluctuations preceding the onset of voluntary action are not (only) spontaneous noise, accumulating based on RP averaging procedures, but also related to a person's breathing cycle that modulates the voluntary movement and the related brain activity.

It was further observed that participants initiated voluntary actions more frequently during the expiration period, and least frequently during the inspiration period. It is assumed that the observed coupling between respiration and voluntary action may occur to reduce the potential competition between two motor commands (i.e., respiration-related motor command vs voluntary motor signal for the finger movement) at the cortical (e.g., SMA) or sub-cortical level (e.g., parabrachial nucleus). In other words, considering that a single breathing cycle is initiated by inspiration and terminated by expiration, participants might have unconsciously preferred to press the button at the end of a single breathing cycle or in between two consecutive breathings.

Relatedly, concerning the EEG data, phase-amplitude coupling was not observed between respiration phase and resting state EEG amplitude, in accordance with previous research reporting that respiration-locked EEG modulations were not observed in central regions (e.g., Cz) when participants are breathing quietly at rest (31). This finding confirms that the coupling between respiration signals and the RP amplitude is not related to artefactual influence of the respiration signal on EEG activity at rest (16). It further suggests such coupling might involve neural interactions between the premotor areas, which are proposed as neural sources of the RP, and other cortical (e.g., the insula, cingulate cortex) or sub-cortical regions (e.g., ventrolateral medulla), which are known to be associated with spontaneous breathing control (32).

In conclusion, it has been shown that spontaneous breathing impacts a fundamental aspect of human self-consciousness and motor cognition, namely voluntary action, as well as one of the most classical EEG components, the RP. The findings provide new insights into the RP by joining two previously disparate fields of neuroscience proposing that 1) the RP is associated with fluctuations of ongoing neuronal activity (4, 7, 8, 9), and that 2) interoceptive processing, in particular processing related to respiration, is an important source of such ongoing neuronal fluctuations. Bridging the gap between these two separate fields it is shown that the RP during self-initiated movements is indeed associated with the fluctuations of ongoing neuronal activity that are driven by the respiratory system.

It is proposed that RP does not correspond to the 'unconscious cerebral initiation of a voluntary action', but at least partly reflects respiration-related cortical processing that is coupled to the onset of voluntary action.

Breathing Affects MI-Based Brain-Computer Interface

Respiration Phase is Coupled with MI Correlates

A spectral analysis was first performed and the topographic map illustrated in FIG. 11 was obtained. Here, it is shown in grand average the power changes when participants were performing the task (t=0 defined as the MI onset). By looking at the topographic mapping of μ and β bands over time, a decrease of power (ERD) can be observed on contralateral channels (C3, CP3). This decrease is happening prominently in the μ band and is present—but weaker—in the β band. Importantly such patterns are starting around 1 s and last until the end of MI.

After ensuring that MI correlates were present in the experiment, a phase coupling analysis was performed to study how the respiratory phase influences the strength of these MI correlates (μ-ERD and β-ERD). It has been found that the MI period was modulated by the respiratory phase (see FIG. 12). Using a permutation test, it has been found that μ band was larger during the late phase of expiration (120°-180°; p=0.039<0.05*, N=1000 permutations). Importantly, the same analysis was also performed on a REST period ([−3 −1] s with respect to onset cue). As a result, the analysis showed that the rest period was not modulated by the respiratory phase (p=0.495, N=1000 permutations).

Respiration Rates Correlated with BMI Accuracies

In this part, it is investigated how the respiration rate changes were linked to decoding performances in distinguishing between MI and REST. To do so, the models were first trained to detect MI on the starting cue of the MI task. These cues were not based on the phase detection algorithm but were set randomly using a jitter. By performing the decoding analysis on these cues, it has been found an accuracy of 62.2%±5.8% (mean±SD), in grand average over the 34 subjects. In FIG. 13A, the average fisher score of each feature in a 2D map (channels×frequencies) is reported. From this map, one can observe that μ and β features were selected to distinguish between MI and REST. The features were principally selected in contralateral channels such as C3. Such results corroborate the previous spectral analysis depicted in FIG. 11. Indeed, the channels and frequencies showing higher fisher scores correspond to the channels and frequencies with the strongest ERDs.

Linear least-squares regression was performed between the respiration rate changes and these decoding performances. It has been found that the decoding performances was predicted from the respiration rate changes (ΔRR) by the following formula:

$$accuracy=0.6+0.73*\Delta RR$$

Note that such measurements were positively correlated (r=0.53, p=0.002<0.01**, df=31, Cohen's d=1.25, BF10=21.05).

A meditation analysis was then performed on the data.

Mediation Effect of β Power

Total Effect

Before analyzing the mediation model, the total effect of ΔRR on classification accuracy was estimated (i.e. path c). With no mediators in the model, the regression coefficient was found statistically significant (path c, β=0.73, p=0.002, 95% CI [0.29, 1.17]). These results are in line with the last results.

Indirect and Direct Effects

Results indicated that β bandpower was significantly predicted by ΔRR (path a21; β=−1.59, p=0.0013 , 95% CI [−2.5, −0.67]). The regression coefficient was not statistically significant for μ bandpower (path a11; β=−1.48, p=0.09>0.05, 95% CI [−3.2, 0.26]). β bandpower was also a significant predictor for classification accuracy controlling for ΔRR (path b21; β=0.38, p=2e-6*, 95% CI [−0.51, −0.25]) while μ bandpower was not able to predict it while controlling for ΔRR (path b11; β=−0.008, p=0.84>0.05, 95% CI [−0.08, −0.07]). Estimated indirect effects (i.e., path a11b11, a21b12) further demonstrated that β bandpower was the only significant mediator between ΔRR and classification accuracy (path a21b12; bootstrapped estimate=0.56, SE=0.20, p=0.012, 95% CI [0.19, 1.01]); path a11b11; bootstrapped estimate=0.014, SE=0.10, p=0.85>0.05, 95% CI [−0.137, 0.357]).

Finally, the direct effect of ΔRR on classification accuracy was estimated, controlling for μ and β bandpower as a mediator (i.e. path c11). The regression coefficient was not found statistically significant (path c11, β=0.16, SE=0.17, p=0.37>0.05, 95% CI [−0.20, 0.51]). These results support a mediation effect of the β bandpower. Importantly, after controlling β bandpower, ΔRR was no longer found as a significant predictor of classification accuracy. No mediation was observed for the μ bandpower. This absence of mediation for μ bandpower can be explained with the features maps in FIG. 13A where visual inspection shows most of the relevant features located in β band.

Inhalation at Task Onset is Associated with Improved MI Detection.

In this analysis, the effect of phase-locked task onset on MI performances during the classification process was investigated. The breathing amplitude over time and the corresponding phase of the starting cue triggered by the respiratory phase detection (FIG. 14A) was first reported. Post-hoc analysis shows that inhalation and exhalation cues were correctly triggered with an average angle of 130.0°±11.9° for the inhalation cues and 291.1°±22.9° for the exhalation cues.

It was also looked at the distribution of the samples used to represent MI class for classification, this was done to ensure that most of the samples were in a given respiratory phase. It has been found that cues were forcing subjects to perform MI in the opposite phase of the detection. For the inhalation cue, MI task was mainly performed during the exhalation phase (221.2°±36.8°) while for the exhalation cue, MI tasks were principally performed during the inhalation phase (135.8°±39.4°). Finally, the post-hoc questionnaire revealed that only 4 participants out of 34 subjects found that cues were triggered by their respiratory phases while 20 thought the cues were delivered randomly. The proportion of subjects who reported that the cues were random was found significantly different from a random distribution (χ2(1,34)=52.5, p=4.3*10−10). This suggests that the subjects did not seem to be aware of the objective of the experiment and then not biased.

Then, a different model was trained for each phase-locked cue type (30 trials for each type, inhale cues vs exhale cues) and computed the TPR for each of these models. Considering the grand average, it was found that the TPR was 60.8%±14.5% for the exhalation cue while being 63.6%±14.7% for the exhalation cue (FIG. 14B). This difference was found significant (paired sample t-test, BF10=1.4, t=2.162, df=33, p=0.038<0.05*, Cohen's d=0.37); meaning that subjects performed better MI during exhalation phase than during inhalation phase. Importantly, although significant, the reported Bayesian Factor (1<BF10<3) implies that even though frequentist statistics show an effect, the Bayes factor suggests more data are needed to conclude a difference of performances between inhalation and exhalation cue. However, this result seems to coincide with FIG. 12 showing stronger MI correlates during exhalation phases and particularly during its late phase.

Finally, the average fisher scores averaged over subjects for each phase-locked cue (see FIG. 15) was also investigated. As can be seen in FIG. 13A, the presence of μ and β features was observed in contralateral channels (C3 channel). Even though the fisher score in μ band seems stronger during the inhale cue with respect to the exhale cue, a multiple paired comparison t-test between the two maps did not show any significant difference.

In this example was investigated how breathing can affect Brain Computer Interfaces based on a Motor Imagery paradigm. Evidence was shown that phase-locked inhalation cues lead to better performance for MI tasks compared to phase-locked exhalation cues and that MI correlates are modulated by the respiratory phases. The analysis focused mainly on the correlates of MI corresponding to a decrease of power in μ and β bands (μ-ERD and β-ERD) and were observed in EEG electrodes over the contralateral cerebral hemisphere.

First, the effect of breathing on MI correlates on BMI performance on these features was investigated. It is shown that the MI correlates are affected by the respiratory phase, with particularly μ-ERD showing a stronger power in the late expiration phase. This is comparable to effects reported in the case of voluntary movement showing a modulation of the cortical readiness potential or RP. Although both data sets (RP and BMI) found a modulation by the respiratory cycle, RP amplitude was found to smaller during expiration (compared to the inhalation; RP data), the BMI study reported stronger μ-ERD during the (late) expiration phase. It is argued that this difference is likely explained by the fact that MI corresponds to an imaginary movement (that shares many similarities with an executed movement), while RPs are found prior to an executed movement and are involved in the initiation of a movement. Accordingly, μ-ERD and RP are inherently different and sequential signals involving different brain regions (RP localized in prefrontal regions involving the supplementary area (SMA) and MI-related μ-ERD localized in contralateral premotor and motor cortex as movement execution).

Second, it is shown that changes in respiration rate during task performance predict BMI performance, making breathing a reliable indicator of BMI ability. Breathing related signals have previously been used to distinguish action success from action failure in several tasks, such as shooting, indicate sport performance, or to distinguish between elite and non-elite athletes. The present data on respiration rate and BMI performance show this effect the first time for BMI performance.

Mediation analysis showed further that the change of respiration rate has an indirect effect on BMI performance and was mediated by the power of β-ERD and thereby reinforces previous proposals that activity of the autonomous nervous system related to breathing control impacts action control and BMI control.

Third, the results suggest that higher BMI performance is phase-locked to inhalation, corroborating previous studies in visuospatial, visual recognition, or memory tasks. Although, these latter results were not supported by Bayesian analysis (indicating the necessity to collect more data), they do corroborate the first finding showing that the subjects are performing better MI during the expiration phase.

In conclusion, the obtained experimental data show that breathing impacts several key human functions, also including the control of a BMI. The data show that breathing affects MI-based BMI and BMI performance and argue that breathing can be considered in the design of a BMI and should be instructed to the subject to foster MI correlates and hence build more accurate BMI. More importantly, breathing is a reliable indicator for BMI performance and should be closely monitored.

Participants

A total of 34 healthy naive subjects (19-32 years, 18 females, right-hand dominant) participated in the experiment.

Protocol

Participants were comfortably seated in front of a PC monitor to perform a task of kinesthetic Motor Imagery (MI). More precisely participants were asked to imagine the feeling associated with performing a movement of their right hand. The experimental protocol is described in FIG. 10. Participants were instructed to stare at a fixation cross during the entire task. Participants were cued by a change of color of the fixation cross indicating the start (fixation cross turning to green) or the end (fixation cross turning to red) of their MI action. In total, participants performed 6 runs of 20 trials. Among these runs, either the starting cue or the stopping cue was based on the respiratory phase (inhalation or exhalation). The respiratory phase was detected in real-time and based on adaptive thresholding. For each run, 10 trials were cued by the inhalation detection while the rest were cued on the exhalation detection. The order of the trials and runs were randomized, and a 1 s-jitter was added to prevent the subject from anticipating the start of the task. Importantly, when the starting cue was based on the respiratory phase, the stopping cue was time-based on it and vice-versa. Subjects were performing the MI task during 5 s. At the end of each trial, participants were able to relax for a period of 4 s. At the end of the experiment, participants were asked to reply to such question ("According to you, how cues were delivered during the experiment?") by choosing one of the following items ("randomly", "muscle activity", "blinking eyes", "heartbeat", "brain activity", "respiration").

Detection of Respiratory Phases in Real-Time

Respiration data were recorded using a respiration belt (Piezo Film Effort Sensor—Kit 1389) placed on the abdomen of the participants. Such data were collected in a 10 s buffer (>2 breathing cycles). A Butterworth filter was used to band-pass filter the breathing data between [0.01-10] Hz. From this 10 s buffer, a threshold was set to 25% of the maximum amplitude for inhalation detection (Eq. 1) or 25% minimum amplitude for exhalation detection (Eq. 2). The maximum and minimum were updated every 62.5 ms.

$$\text{threshold}_{inhalation} = 0.25 * \text{max}_{buffer} \qquad \text{(Eq. 1)}$$

$$\text{threshold}_{exhalation} = 0.25 * \text{min}_{buffer} \qquad \text{(Eq. 2)}$$

The last time point was then compared to the two thresholds which in results triggered the cues.

ERD/S Computation

A spectral analysis was performed to compute the event-related spectral perturbations (ERSP). In this analysis, the power was calculated with the following equation and averaged over subjects:

$$\frac{ERD}{ERS} = 10 * \log\left(\frac{A}{B}\right) \qquad \text{(Eq. 3)}$$

Where A represents the power activity for a frequency of interest at a given time and B represents the average power during a baseline interval, chosen between [−2, 0] with respect to the starting cue.

A topographic map was plotted for each frequency band of interest: μ [8-12] Hz and β [13-30] Hz.

Post-Hoc Respiratory Phase

Respiration data were band-pass filtered between [0.01-10] Hz. The respiratory phase was calculated by applying a Hilbert transform and taking the angle of the complex argument. For the phase coupling analysis, the respiratory phase was binned into six equally sized bins.

Respiration Rate Changes

Using the respiratory filtered signal, the respiration rate (RR) defined as the number of breaths taken per minute was computed for each subject. For each subject, the RR was averaged over the two time-intervals: one between [−2, 0] s and the other between [1, 3] s with respect to the onset of MI task and respectively representing REST and MI periods. Finally, the RR change (ΔRR) between these two periods was calculated as follows:

$$\Delta RR = RR_{REST} - RR_{MI}$$

with RR the number of respiration cycle per minute.

From these data, the interquartile range (IQR) was calculated as well as the first and third quartiles (Q1, Q3) and removed outliers if ΔRR was not within [Q1−1.5*IQR, Q3+1.5*IQR].

Phase Coupling Analysis

To perform phase the coupling analysis, a zero-phase bandpass was applied to each channel within [8-12] Hz for μ band and within [13-30] Hz for β band. From the filtered signals, a Hilbert transform was applied to extract the envelope of the signal. From such an envelope, the power was computed for each channel from which was subtracted the average power over a baseline interval chosen between [−3, −1] s with respect to the onset. The average power was calculated over the 15 selected channels (Fz, FC3, FC1, FCz, FC2, FC4, C3, C1, Cz, C2, C4, CP3, CP1, CP2) corresponding to the electrodes of interest for MI tasks. The data were then epoched and the z-scores normalized over the trials.

Two time-intervals (between [1, 4] s and [−3, −1] s) were chosen to represent respectively the period of MI and REST. From each trial, the respiratory phase was computed for each time point. The band power of μ and β bands were averaged over all the time points and grouped in the same bin of the respiratory phase on these given intervals.

Additionally, a topographic map was plotted for each frequency band of interest (μ [8-12] Hz and β [13-30] Hz) with respect to the binned respiratory phase.

For each subject, the modulation index was calculated on average over trials for each permutation. This modulation index is a measure that quantifies the deviation of a defined amplitude distribution from a uniform distribution. Then, the modulation index of each subject was averaged to obtain a grand average modulation index.

Decoding Analysis

Features Extraction

Power spectral densities (PSD) were computed in a 1 s-window based on Thomson's multitaper power spectral density (PSD) estimation from 8 to 30 Hz with a 1 Hz resolution on the 15 channels of interest, yielding a total of 345 features.

Cross-Validation Process

A nested cross-validation (CV) based on 5 folds in which the number of features used to build each model from each fold was fine-tuned. Importantly, these 5-folds were trial-based to prevent samples overlapping between training and testing sets. Trials were split into different folds based on their chronological order. For each fold, a diagonal Linear Discriminant Analysis (diag-LDA) classifier was trained to distinguish between the two time-intervals [−2, 0] s (REST) and [1, 3] s (MI) with respect to the onset cue (t=0). The time interval of the MI class was set based on the latency of MI correlates.

Feature Selection

To fine-tune the number of features, inside each fold, an inner 5-fold CV in which the number of features varied between 1 and 50 was performed. The optimal number of features was chosen when minimizing the averaged misclassification over the inner CV. The features were selected based on the amount of information they provided to discriminate between the two classes. This was computed using the Fisher Score.

Classification Metrics

To assess the classification performance, the accuracy at the sample level over the 10-fold cross-validation was calculated. Here, a sample corresponds to a 1 s-window. The accuracy was defined as the number of correctly classified samples over the total number of samples and was computed for each fold. The True Positive Rate (TPR) for Motor Imagery was also computed, such measure corresponds to the number of correct detections within the MI class.

Statistical Analysis

Paired Sample t-Test

To compare BMI performances between inhale-locked cues and exhale-locked cues, the average accuracies of the 5-fold models were calculated for each subject and each type of cue. A paired sample t-test was then performed comparing all the average accuracies for inhale-locked cues and exhale-locked cues.

Regression and Correlation

After calculating ΔRR on a trial-based level, the average ΔRR over trials for each subject was computed. Using the BMI performances obtained from the non-phase locked cues, the average BMI accuracies as well for each subject were calculated. A linear least regression was then performed on the average BMI accuracies with the average ΔRR as a predictor. With these data, a correlation was performed as well.

Permutation Test

For each subject, the band power for each bin and trial were randomly permuted (N=1000). For each permutation, the modulation index was calculated. Based on the 1000 permutations, a distribution of the modulation index was found and averaged over subjects. This distribution was compared with the real grand average modulation index. A p-value was calculated from this comparison.

Bayesian Analysis

To reinforce the interpretation of the results, Bayesian Paired Samples t-tests and Bayesian correlations was performed, using JASP software (version 0.13.1.0). For each test, the Bayesian factor (BF10) was reported. Having a BF10 value smaller than ⅓ indicates substantial evidence supporting the null hypothesis (H0) while a BF10 value greater than 3 is considered as substantial evidence supporting the alternative hypothesis (H1). A BF10 value between ⅓ and 3 means that the data is insensitive and that more data are needed to conclude.

Mediation Analysis

Figure 16:
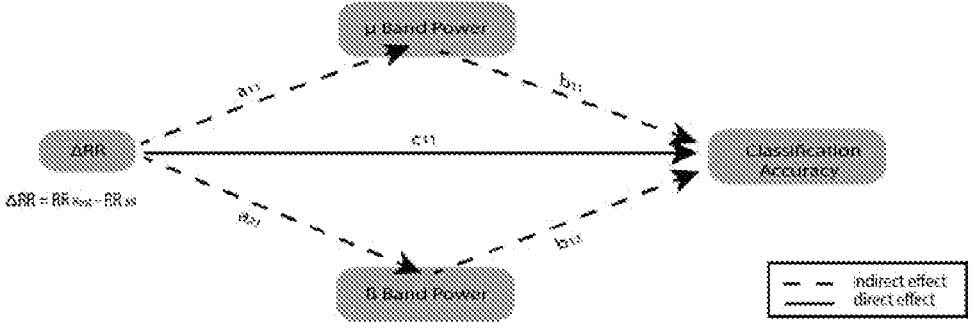

To investigate the effect of change of respiration rate (ΔRR) on the classification accuracy, a mediation analysis was performed on the data (see FIG. 16). In this model, it was investigated whether μ and β band power mediated the relationship between ΔRR and classification accuracy. It was estimated that: (1) the total effect of ΔRR on classification accuracy (path c); (2) the direct effect of the model mediated by μ and β band power (path c'11); and (3) the indirect effect of the model (paths a11b11, a21b12). Models were tested using an approach that allows simple and multiple mediators to be included in the analysis. First, classic mediation criteria were tested: (1) The predictor predicts the outcome—path c; (2) The predictor predicts the mediator—path a; (3) The mediator predicts the outcome while controlling for the predictor—path b. Finally, statistical significance of the direct and indirect effects were estimated using a bootstrapping method. To avoid biased estimations under conditions of non-normality, bias-corrected confidence intervals (95%) were obtained with 1000 bootstrap resamples.

While the invention has been disclosed with reference to certain preferred embodiments, numerous modifications, alterations, and changes to the described embodiments, and equivalents thereof, are possible without departing from the sphere and scope of the invention. Accordingly, it is intended that the invention not be limited to the described embodiments, and be given the broadest reasonable interpretation in accordance with the language of the appended claims.

REFERENCES

1. Fried I, Mukamel R, Kreiman G. Internally generated preactivation of single neurons in human medial frontal cortex predicts volition. Neuron 69, 548-562 (2011).
2. Haggard P. Human volition: towards a neuroscience of will. Nat. Rev. Neurosci. 9, 934-946 (2008).
3. Kornhuber H H, Deecke L. Changes in brain potentials with willful and passive movements in humans: The readiness potential and reafferent potentials. Pflugers Arch. 284, 1-17 (1965).
4. Murakami M, Vicente M I, Costa G M, Mainen Z F. Neural antecedents of self-initiated actions in secondary motor cortex. Nat. Neurosci. 17, 1574-1582 (2014).
5. Libet B, Gleason C A, Wright E W, Pearl D K. Time of conscious intention to act in relation to onset of cerebral activity (readiness-potential). The unconscious initiation of a freely voluntary act. Brain 106 (Pt 3), 623-642 (1983).
6. Libet B. Unconscious Cerebral Initiative and the Role of Conscious Will in Voluntary Action. Behav. Brain Sci. 8, 529-539 (1985).
7. Khalighinejad N, Schurger A, Desantis A, Zmigrod L, Haggard P. Precursor processes of human self-initiated action. NeuroImage 165, 35-47 (2018).
8. Schurger A, Mylopoulos M, Rosenthal D. Neural Antecedents of Spontaneous Voluntary Movement. A New Perspective. Trends Cogn. Sci. 20, 77-79 (2016).
9. Schurger A, Sitt J D, Dehaene S. An accumulator model for spontaneous neural activity prior to self-initiated movement. Proc. Natl. Acad. Sci. U.S.A. 109, E2904-E2913 (2012).
10. Park H D, Correia S, Ducorps A, Tallon-Baudry C. Spontaneous fluctuations in neural responses to heartbeats predict visual detection. Nat. Neurosci. 17, 612-618 (2014).
11. Garfinkel S N, Minati L, Gray M A, Seth A K, Dolan R J, Critchley H D. Fear from the heart: sensitivity to fear stimuli depends on individual heartbeats. J. Neurosci. 34, 6573-6582 (2014).

12. Ohl S, Wohltat C, Kliegl R, Pollatos O, Engbert R. Microsaccades Are Coupled to Heartbeat. J. Neurosci. 36, 1237-1241 (2016).
13. Park H D, et al. Neural Sources and Underlying Mechanisms of Neural Responses to Heartbeats, and their Role in Bodily Self-consciousness: An Intracranial EEG Study. Cereb. Cortex 28, 2351-2364 (2018).
14. Rebollo I, Devauchelle A D, Beranger B, Talton-Baudry C. Stomach-brain synchrony reveals a novel, delayed-connectivity resting-state network in humans. eLife 7, (2018).
15. Tort A B L, Brankack J, Draguhn A. Respiration-Entrained Brain Rhythms Are Global but Often Overlooked. Trends Neurosci. 41, 186-197 (2018).
16. Birn R M, Murphy K, Bandettini P A. The effect of respiration variations on independent component analysis results of resting state functional connectivity. Hum. Brain Mapp. 29, 740-750 (2008).
17. Evans K C, Shea S A, Saykin A J. Functional MRI localisation of central nervous system regions associated with volitional inspiration in humans. J. Physiol. 520 Pt 2, 383-392 (1999).
18. Bramble D M, Carrier D R. Running and breathing in mammals. Science 219, 251-256 (1983).
19. Moore J D, et al. Hierarchy of orofacial rhythms revealed through whisking and breathing. Nature 497, 205-210 (2013).
20. Pfurtscheller G, Ortner R, Bauernfeind G, Linortner P, Neuper C. Does conscious intention to perform a motor act depend on slow cardiovascular rhythms? Neurosci. Lett. 468, 46-50 (2010).
21. Ball T, Schreiber A, Feige B, Wagner M, Lucking C H, Kristeva-Feige R. The role of higher-order motor areas in voluntary movement as revealed by high-resolution EEG and fMRI. NeuroImage 10, 682-694 (1999).
22. Azevedo R T, Garfinkel S N, Critchley H D, Tsakiris M. Cardiac afferent activity modulates the expression of racial stereotypes. Nat. Commun. 8, 13854 (2017).
23. Kurnikova A, Moore J D, Liao S M, Deschenes M, Kleinfeld D. Coordination of Orofacial Motor Actions into Exploratory Behavior by Rat. Curr. Biol. 27, 688-696 (2017).
24. Zelano C, et al. Nasal Respiration Entrains Human Limbic Oscillations and Modulates Cognitive Function. J. Neurosci. 36, 12448-12467 (2016).
25. Mitrou N, Laurin A, Dick T, Inskip J. A peak detection method for identifying phase in physiological signals. Biomed. Signal Process. Control 31, 452-462 (2017).
26. Mineva A, Popivanov D. Method for single-trial readiness potential identification, based on singular spectrum analysis. J. Neurosci. Methods 68, 91-99 (1996).
27. Richter C G, Babo-Rebelo M, Schwartz D, Tallon-Baudry C. Phase-amplitude coupling at the organism level: The amplitude of spontaneous alpha rhythm fluctuations varies with the phase of the infra-slow gastric basal rhythm. NeuroImage 146, 951-958 (2017).
28. Tort A B, Komorowski R, Eichenbaum H, Kopell N. Measuring phase-amplitude coupling between neuronal oscillations of different frequencies. J. Neurophysiol. 104, 1195-1210 (2010).
29. Smotherman M, Kobayasi K, M a J, Zhang S, Metzner W. A mechanism for vocal-respiratory coupling in the mammalian parabrachial nucleus. J. Neurosci. 26, 4860-4869 (2006).

30. Paydarfar D, Gilbert R J, Poppel C S, Nassab P F. Respiratory phase resetting and airflow changes induced by swallowing in humans. J. Physiol. 483 (Pt 1), 273-288 (1995).

31. Raux M, et al. Electroencephalographic evidence for pre-motor cortex activation during inspiratory loading in humans. J. Physiol. 578, 569-578 (2007).

32. Del Negro C A, Funk G D, Feldman J L. Breathing matters. Nat. Rev. Neurosci. 19, 351-367 (2018).

33. Allard E, et al. Interferences between breathing, experimental dyspnoea and bodily self-consciousness. Sci. Rep. 7, 9990 (2017).

34. Morawiec E, Raux M, Kindler F, Laviolette L, Similowski T. Expiratory load compensation is associated with electroencephalographic premotor potentials in humans. J. Appl. Physiol. 118, 1023-1030 (2015).

35. McFarland D H. Respiratory markers of conversational interaction. J. Speech Lang. Hear. Res. 44, 128-143 (2001).

36. Faull O K, Subramanian H H, Ezra M, Pattinson K T S. The midbrain periaqueductal gray as an integrative and interoceptive neural structure for breathing. Neurosci. Biobehav. Rev. 98, 135-144 (2019).

37. Baek K, et al. Impaired awareness of motor intention in functional neurological disorder: implications for voluntary and functional movement. Psychol. Med. 47, 1624-1636 (2017).

38. Oostenveld R, Fries P, Maris E, Schoffelen J M. Field-Trip: Open source software for advanced analysis of MEG, EEG, and invasive electrophysiological data. Comput. Intell. Neurosci. 2011, 156869 (2011).

39. Garipelli G, Chavarriaga R, Millan J D. Single Trial Recognition of Anticipatory Slow Cortical Potentials: The Role of Spatio-Spectral Filtering. 5th International Ieee/Embs Conference on Neural Engineering, 408-411 (2011).

40. Schultze-Kraft M, et al. The point of no return in vetoing self-initiated movements. Proc. Natl. Acad. Sci. U.S.A. 113, 1080-1085 (2016).

41. Ajne B. A Simple Test for Uniformity of a Circular Distribution. Biometrika 55, 343-354 (1968).

40. Berens P. CircStat: A MATLAB Toolbox for Circular Statistics. J. Stat. Softw. 31, 1-21 (2009).

The invention claimed is:

1. A method for determining an intention of performing a voluntary action in a living subject, the method comprising:

obtaining neuroelectrical signals from the subject using one of an electroencephalogram (EEG) system, an electrocorticography (ECoG) system, a magnetoencephalography (MEG) system, and an event-related potential (ERP) detector, the neuroelectrical signals including one of a Readiness Potential (RP) amplitude signal and μ- and/or β-Event-Related-Desynchronization μ-ERDs/β-ERDs power measurement;

obtaining respiratory signals from the subject using a respiration detector, the respiratory signals including an expiration phase signal;

comparing the RP amplitude signal and/or the μ-ERDs/β-ERDs power measurement with the respiratory signals within a time-window, to obtain a time-based correlation between the RP amplitude, and/or the μ-ERDs/β-ERDs power measurement, and the respiratory signals; and outputting the time-based correlation between the RP amplitude, and/or the α-ERDs/β-ERDs power measurement, and the respiratory signals to indicate the intention of performing the voluntary action based on the comparing the RP amplitude signal and/or the μ-ERDs/β-ERDs power measurement with the respiratory signals, wherein a smaller RP amplitude signal corresponding to an expiration phase of the respiratory signals, and/or a power decrease of μ- and/or β-Event-Related Desynchronization corresponding to the expiration phase of the respiratory signals is indicative of the intention of performing the voluntary action.

2. The method of claim 1, further comprising:

confirming the intention of performing the voluntary action when the RP amplitude signal is smaller in the expiration phase of the expiration phase signal then in an inspiratory phase of the respiratory phrase signal, and/or when α-ERDs/β-ERDs power measurement decreases.

3. The method of claim 1, wherein the neuroelectrical signals include EEG-derived signals.

4. The method of claim 1, wherein the respiratory signals are obtained by measuring at least one of changes in thoracic circumference, abdominal circumference, nasal air flows, and/or electrical potential on a body surface of the living being during respiration.

5. The method of claim 1, wherein the time-based correlation is obtained by superposing the RP amplitude signal and/or the μ-ERDs/β-ERDs power measurement with the respiratory signals in real time.

6. The method of claim 1, wherein the RP amplitude and/or the μ-ERDs/β-ERDs power is averaged depending on respiration portions of a respiration phase correlation between RP amplitude and/or the μ-ERDs/β-ERDs power is quantified.

7. The method of claim 1, wherein the living subject suffers from at least one of a muscular disease, a neurological disease, a respiratory disease, and/or a psychiatric disorder.

8. A system comprising:

an electroencephalogram (EEG) system or an electrocorticography (ECoG) system or a magnetoencephalography (MEG) system or an event-related potential (ERP) detector configured to obtain neuroelectrical signals from a living subject, the neuroelectrical signals comprising a RP amplitude signal and/or a μ-ERDs/β-ERDs power measurement;

a respiration detector configured to obtain respiratory signals from the living subject, the respiratory signals including an expiration phase signal; and a computer configured to execute instructions to:

obtain the neuroelectrical signals from the subject using one of the electroencephalogram (EEG) system, the electrocorticography (ECoG) system, the magnetoencephalography (MEG) system, and the event-related potential (ERP) detector, the neuroelectrical signals including one of a Readiness Potential (RP) amplitude signal and μ- and/or β-Event-Related-Desynchronization μ-ERDs/β-ERDs power measurement, obtain the respiratory signals from the subject using the respiration detector, the respiratory signals including the expiration phase signal, compare the RP amplitude signal and/or the μ-ERDs/β-ERDs power measurement with the respiratory signals within a time-window, to obtain a time-based correlation between the RP amplitude, and/or the μ-ERDs/β-ERDs power measurement, and the respiratory signals; and output the time-based correlation between the RP amplitude, and/or the μ-ERDs/β-ERDs power measurement, and the respiratory signals to indicate the intention of performing the voluntary action based on the comparing the RP amplitude signal and/or the μ-ERDs/β-ERDs power measurement with the respiratory signals, wherein a smaller RP amplitude signal corresponding to an expiration phase of the respiratory signals, and/or a power decrease of μ- and/or β-Event-Related Desynchronization corresponding to the expiration phase of the respiratory signals is indicative of the intention of performing a voluntary action.

9. The system of claim 8, wherein the device configured to obtain respiratory signals includes at least one of a respiratory belt, a nasal spirometer, a plurality of electrodes, and/or video recording device.

10. The system of claim 8, wherein the computer is further configured to execute instructions to actuate an external device based on the time-based correlation between respiratory signals and at least one of the RP amplitude signal and the μ-ERDs/β-ERDs power measurement.

\* \* \* \* \*